(12) United States Patent
Nino et al.

(10) Patent No.: US 12,121,343 B2
(45) Date of Patent: *Oct. 22, 2024

(54) FOOT-MOUNTED SENSOR SYSTEMS FOR TRACKING BODY MOVEMENT

(71) Applicant: Reflx Labs, Inc., Kent, WA (US)

(72) Inventors: Giovanni Nino, Issaquah, WA (US); Jose Torres, Jr., Seattle, WA (US); Tyler Blumenthal, Renton, WA (US); Phillip Dewayne Bondurant, Covington, WA (US); Vincent Fratello, Bellevue, WA (US); Christian Robert Lentz, Benton City, WA (US)

(73) Assignee: Reflx Labs, Inc., Kent, WA (US)

( * ) Notice: Subject to any disclaimer, the term of this patent is extended or adjusted under 35 U.S.C. 154(b) by 1028 days.

This patent is subject to a terminal disclaimer.

(21) Appl. No.: 16/983,421

(22) Filed: Aug. 3, 2020

(65) Prior Publication Data

US 2020/0375496 A1    Dec. 3, 2020

Related U.S. Application Data

(63) Continuation of application No. 16/403,052, filed on May 3, 2019, now Pat. No. 10,729,356, which is a
(Continued)

(51) Int. Cl.
*G06F 3/033* (2013.01)
*A43B 3/34* (2022.01)
(Continued)

(52) U.S. Cl.
CPC ............... *A61B 5/103* (2013.01); *A43B 3/34* (2022.01); *A61B 5/02444* (2013.01);
(Continued)

(58) Field of Classification Search
CPC ... A61B 5/103; A61B 5/02444; A61B 5/1038; A61B 5/6807; A61B 5/021;
(Continued)

(56) References Cited

U.S. PATENT DOCUMENTS 4,134,063 A    1/1979  Nicol et al.
4,314,228 A    2/1982  Eventoff
(Continued)

FOREIGN PATENT DOCUMENTS

TW    201233382 A    8/2012
WO    2009152456 A2    12/2009

OTHER PUBLICATIONS

"Force Sensors for Design," eBook produced by Machine Design Custom Media, Tekscan website, <https://www.tekscan.com/flexiforce-e-book-force-sensors-design-download>, 9 pages.
(Continued)

*Primary Examiner* — Kristina M Deherrera
*Assistant Examiner* — Fatemeh Esfandiari Nia
(74) *Attorney, Agent, or Firm* — CHRISTENSEN O'CONNOR JOHNSON KINDNESS PLLC

(57) ABSTRACT

A method is disclosed for foot sensors to be used to determine at least two characteristics of a subject's activity by using a combination of sensors for force and foot orientation/motion/position. A wearable footwear ecosystem is comprised of the subject's footwear, sensor-enabled insoles or insertable devices, in- or on-footwear electronics that is hard wired to the sensors and may contain additional sensors such as accelerometers, a master device and means to communicate (typically wirelessly) among the various sensor platforms, and the master device including clock synchronization. Correlating the time stamps for data among various sensors, and the master device communicating wirelessly is critical to accurate determination of the desired
(Continued)

characteristics. Multiple force-sensitive resistors on a common substrate are individually optimized for dynamic range. Pulse sensors using arrays of such force-sensitive resistors are implemented. The resultant system can profitably be used for gaming, biometric monitoring, and activity tracking.

20 Claims, 18 Drawing Sheets

Related U.S. Application Data continuation of application No. 14/742,473, filed on Jun. 17, 2015, now Pat. No. 10,307,081, which is a continuation of application No. PCT/US2013/075879, filed on Dec. 17, 2013.

(60) Provisional application No. 61/894,833, filed on Oct. 23, 2013, provisional application No. 61/747,118, filed on Dec. 28, 2012, provisional application No. 61/738,191, filed on Dec. 17, 2012.

(51) Int. Cl.
*A61B 5/00* (2006.01)
*A61B 5/024* (2006.01)
*A61B 5/103* (2006.01)
*A63F 13/212* (2014.01)
*A63F 13/218* (2014.01)
*A63F 13/50* (2014.01)
*G01G 19/44* (2006.01)
*G06F 3/01* (2006.01)
*A42B 3/04* (2006.01)
*A61B 5/021* (2006.01)
*A61B 5/11* (2006.01)

(52) U.S. Cl.
CPC .......... *A61B 5/1038* (2013.01); *A61B 5/6807* (2013.01); *A63F 13/212* (2014.09); *A63F 13/218* (2014.09); *A63F 13/50* (2014.09); *G06F 3/011* (2013.01); *G06F 3/0334* (2013.01); *A42B 3/046* (2013.01); *A61B 5/021* (2013.01); *A61B 5/02438* (2013.01); *A61B 5/1112* (2013.01); *A61B 5/1118* (2013.01); *A61B 5/1123* (2013.01); *A61B 5/6803* (2013.01); *A61B 5/6895* (2013.01); *A61B 5/6898* (2013.01); *A61B 2562/0219* (2013.01); *A61B 2562/0247* (2013.01); *A61B 2562/0271* (2013.01); *A61B 2562/046* (2013.01); *A63C 2203/18* (2013.01); *A63C 2203/24* (2013.01); *A63F 2300/1012* (2013.01); *G01G 19/44* (2013.01)

(58) Field of Classification Search
CPC . A61B 5/02438; A61B 5/1112; A61B 5/1118; A61B 5/1123; A61B 5/6803; A61B 5/6895; A61B 5/6898; A61B 2562/0219; A61B 2562/0247; A61B 2562/0271; A61B 2562/046; A43B 3/34; A43B 3/44; A63F 13/212; A63F 13/218; A63F 13/50; A63F 2300/1012; G06F 3/011; G06F 3/0334; A42B 3/046; A63C 2203/18; A63C 2203/24; G01G 19/44
See application file for complete search history.

(56) References Cited

U.S. PATENT DOCUMENTS

| | | | |
|---|---|---|---|
| 4,739,299 | A | 4/1988 | Eventoff et al. |
| 5,899,963 | A | 5/1999 | Hutchings |
| 6,122,960 | A | 9/2000 | Hutchings et al. |
| 6,307,168 | B1* | 10/2001 | Newham ............. H01H 3/141 |
| | | | 200/86 R |
| 6,836,744 | B1 | 12/2004 | Asphahani et al. |
| 7,921,716 | B2 | 4/2011 | Morris Bamberg et al. |
| 8,217,788 | B2 | 7/2012 | Vock et al. |
| 8,249,831 | B2 | 8/2012 | Vock |
| 8,375,784 | B2 | 2/2013 | Bamberg et al. |
| 8,627,716 | B2 | 1/2014 | Son |
| 9,224,291 | B2 | 12/2015 | Moll-Carrillo et al. |
| 10,307,081 | B2* | 6/2019 | Nino ....................... A63F 13/50 |
| 10,729,356 | B2* | 8/2020 | Nino ....................... A43B 3/44 |
| 2003/0009308 | A1 | 1/2003 | Kirtley |
| 2006/0143645 | A1 | 6/2006 | Vock et al. |
| 2008/0167580 | A1 | 7/2008 | Avni et al. |
| 2009/0267783 | A1 | 10/2009 | Vock et al. |
| 2010/0063779 | A1 | 3/2010 | Schrock et al. |
| 2011/0054359 | A1 | 3/2011 | Sazonov |
| 2011/0098605 | A1 | 4/2011 | deGreef et al. |
| 2011/0301504 | A1 | 12/2011 | Lan et al. |
| 2012/0086550 | A1* | 4/2012 | LeBlanc ................ G07C 9/37 |
| | | | 340/5.82 |
| 2012/0212505 | A1 | 8/2012 | Burroughs et al. |
| 2012/0291563 | A1 | 11/2012 | Schrock et al. |
| 2013/0185003 | A1 | 7/2013 | Carbeck et al. |
| 2013/0192071 | A1 | 8/2013 | Esposito et al. |
| 2014/0033572 | A1 | 2/2014 | Steier et al. |
| 2020/0297064 | A1* | 9/2020 | Molyneux ............ A43B 13/122 |

OTHER PUBLICATIONS

"FSR101—Force Sensing Resistor Theory and Applications," Sensitronics LLC website, <http://www.sensitronics.com/pdf/Sensitronics_FSR_101.pdf> [retrieved Oct. 24, 2016], 15 pages.

"FSR101—The Basics," Sensitronics LLC website, <https://web.archive.org/web/20121028114449/http://www.sensitronics.com/fsr101.htm> [retrieved Oct. 28, 2012], 4 pages.

"Tutorials: Force Sensing Linear Potentiometers," Sensitronics LLC website, <http://www.sensitronics.com/tutorials/force-sensing-linear-potentiometer/page2.php> [retrieved Oct. 24, 2016], 2 pages.

"Tutorials: XYZ Pad Example," Sensitronics LLC website, <http://www.sensitronics.com/tutorials/xyz-pad/page2.php> [retrieved Oct. 24, 2016], 2 pages.

Cavanaugh, P.R., et al., "In-Shoe Plantar Pressure Measurement: A Review," The Foot 2(4):185-194, Dec. 1992.

International Preliminary Report on Patentability mailed Jun. 23, 2015, issued in corresponding International Application No. PCT/US2013/075879, filed Dec. 17, 2013, 10 pages.

International Search Report and Written Opinion mailed Apr. 10, 2014, issued in corresponding International Application No. PCT/US2013/075879, filed Dec. 17, 2013, 14 pages.

Morris, S.J., "A Shoe-Integrated Sensor System for Wireless Gait Analysis and Real-Time Therapeutic Feedback," doctoral thesis, Massachusetts Institute of Technology, Cambridge, Massachusetts, Jun. 2004, 314 pages.

Official Letter and Search Report mailed Jul. 20, 2016, issued in TW 103120726, filed Jun. 16, 2014, 35 pages.

Orlin, M.N., and T.G. McPoil, "Plantar Pressure Assessment," Physical Therapy 80(4):399-409, Apr. 2000.

Razak, A.H.A, et al., "Foot Plantar Pressure Measurement System: A Review," Sensors 12(7):9884-9912, Jul. 2012.

Redd, C.B., and S.J.M. Bamberg, "A Wireless Sensory Feedback Device for Real-Time Gait Feedback and Training," IEEE/ASME Transactions on Mechatronics 17(3):425-433, Jun. 2012.

(56) References Cited

OTHER PUBLICATIONS

Zhu, H., et al., "An Umbilical Data-Acquisition System for Measuring Pressures Between the Foot and the Shoe," IEEE Transactions on Biomedical Engineering 37(9):908-911, Sep. 1990.

\* cited by examiner

FOOT-MOUNTED SENSOR SYSTEMS FOR TRACKING BODY MOVEMENT

CROSS-REFERENCE(S) TO RELATED APPLICATIONS

This application is a continuation of U.S. patent application Ser. No. 16/403,052, filed May 3, 2019, which is a continuation of U.S. patent application Ser. No. 14/742,473, filed Jun. 17, 2015, which is a continuation of PCT/US2013/075879, filed Dec. 17, 2013, which claims the benefit of U.S. Provisional Patent Application No. 61/894,833, filed Oct. 23, 2013, U.S. Provisional Patent Application No. 61/747,118, filed Dec. 28, 2012, and U.S. Provisional Patent Application No. 61/738,191, filed Dec. 17, 2012. Each of the disclosures of said applications are incorporated by reference herein in their entirety.

BACKGROUND

Instrumented shoes, foot sensors, and gait analysis systems are present to a limited extent in published literature and the marketplace. Existing systems primarily consist of 1) simple activity sensors that give distance and rate of motion, 2) large and complex clinical systems suitable only for a laboratory, doctor's office, or shoe store, and 3) instrumented insoles.

Biomechanical motion has been analyzed in laboratory facilities using complex optical sensing systems and in medical offices with clinicians making visual qualitative observations of the subject's gait. Commercial technologies for plantar pressure assessment including the Emed Sensor Platform and Pedar Insole System by Novel Electronics, Inc., of St. Paul, Minn., United States; F-Scan System by Tekscan, Inc., of Boston, Mass. United States; and the Musgrave Footprint System by WM Automation and Preston Communication, Ltd., of North Wales, United Kingdom. In these technologies, a fine grain matrix array of sensors measures force when the foot contacts the sensor. Systems of this type are bulky, expensive and not practical for a consumer outside of a laboratory setting.

Prior art discrete in-shoe sensors located at designed anatomical points are obtrusive and irritating to a user, have edge effects between the sensor material and the surrounding insole, are subject to motion in the shoe resulting from shear stress, are subject to mechanical damage at the electrical connections, may be distorted by the contoured shape of the sole, and sensor performance may be affected by humidity and heat such that the recorded values may not accurately reflect the pressure experienced by these anatomical points in an un-instrumented shoe.

Researchers have used force-sensitive resistors (FSRs) at the five metatarsal heads, big toe, and heel in a tethered system for gait analysis, but the wires of such systems are unduly obtrusive and do not allow field testing. Examples include U.S. Pat. Nos. 5,899,963 and 6,122,960, issued to Hutchings et al.

Other researchers have pointed out the need for an inexpensive in-shoe system for gait analysis and utilized three orthogonal accelerometers, three orthogonal gyroscopes, four force-sensitive resistor plantar pressure sensors in a removable insole, two bend sensors, dynamic pressure sensors, and electric field height sensors. The objective of the GaitShoe was to 1) make no change in the gait, 2) characterize the motion of both feet, 3) be untethered, and 4) use the subjects' own shoes. In the GaitShoe, the FSRs were located at the medial (first) and lateral (fifth) metatarsal heads and medial and lateral sides of the heel pads. Radio-frequency (RF) transmission was used to send the data to a computer. U.S. Pat. No. 6,836,744, issued to Asphahani et al. ("Asphahani"), involves a similar system to the Gaitshoe. Asphahani also discloses sensors that are removable from a shoe.

U.S. Pre-Grant Publication No. 2011/0054359, by Sazonov et al. ("Sazonov"), discloses an activity sensor directed to weight-management applications. Sazonov discloses "A footwear system for monitoring weight, posture allocation, physical activity classification and energy expenditure" specifically comprising an accelerometer, pressure sensing device, and transmitter. In Sazonov, data from sensing device is sent wirelessly to a controlling device such as a smart phone. However, Sazonov discloses sending data to a controlling device in a burst mode so that the wireless network receiver and the transmitter can be powered off for a majority of time to reduce power consumption. For example, data is transmitted using a Bluetooth transceiver such as in the Nike+ Sport Sensor by Nike. Burst mode transmission involves data received by the receiver that is not synchronized with the sensor. If there are multiple sensors as between both a subject's feet or among multiple subjects, the data from each sensor is uncorrelated in time and, therefore, the data is not very useful for determining body mechanics.

The prior art discloses measuring pressure on the plantar surface of the foot using FSR, force sensitive capacitors, piezoelectric transducers, and other means. However, instrumented shoe systems beyond relatively simple pedometers are notably absent from the marketplace. In particular, it is believed that instrumented shoes for gaming applications are also absent from any literature. Rather, gaming applications have relied on external instrumented platforms such as the Nintendo Wii Fit Balance Board and Dance Dance Revolution's Dance Pad.

An FSR, as disclosed in U.S. Pat. No. 4,314,228, issued to Eventoff et al. ("Eventoff I"), which is hereby incorporated by reference in its entirety, is a device that measures force through the amount of contact between two parallel surfaces separated by an air gap produced by a spacer between the two surfaces imprinted in various patterns with a resistive semiconducting material conducting material. The greater the force between the surfaces, the more the air gap is closed, increasing the physical contact between the surfaces and decreasing the resistance of the device. In a thru mode FSR configuration, both substrates are printed with a connectorized conductive pad and overprinted with a semiconducting FSR material and faced toward each other separated by a spacer layer with a central hole so the conductivity is established by force between the two substrates. In a shunt mode FSR configuration, the FSR includes one substrate printed with a semiconducting FSR material, and a second layer imprinted with two connectorized sets of interdigitated electrodes separated by a spacer so the conductivity is established by force that increases the contact of the electrodes with the FSR layer thereby increasing the conductivity of one set of electrodes to the other through the semiconducting material. The three layers comprising a shunt mode design are shown in FIG. 1.

Dots of dielectric material may be placed on one surface or another to impede the surfaces from coming together. The air gap must be vented in some way to allow the two surfaces to come together. This, however, creates problems because the resistive characteristics of the commercial resistive materials, such as molybdenum disulfide, change with humidity. Thus, an FSR could be rendered completely inoperable by immersion in liquid, such as water.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

One aspect of the present subject matter includes a method of determining two or more characteristics of an activity performed by a subject. The method comprises providing a sensor system. The sensor system includes two separate foot sensor subsystems, each including two or more sensor devices selected from the group consisting of: a force sensor, an accelerometer, and a gyroscope. Each foot sensor subsystem is configured to generate time-stamped device data that includes a relative time that the device data was generated. Each of the foot sensor subsystems is configured to be coupled to a separate foot of the subject. The system also includes a data processor system in communication with both of the foot sensor subsystems and located separate from at least one of the foot sensor subsystems. The method also includes generating time-stamped activity data during the activity for each foot sensor subsystem based on the time-stamped device data output, communicating the time-stamped activity data for each foot sensor subsystem to the data processor system, correlating the time-stamped activity data from each foot sensor subsystem to provide correlated activity data using the data processor system, and determining two or more characteristics of the activity of the subject using the correlated activity data using the data processor system.

In one embodiment, each foot sensor subsystems further includes a clock for deriving the time stamps of individual devices, where each clock is synchronized by communication with a master device. In another embodiment, the data processor system includes a display device. In another embodiment, the two or more characteristics are selected from the group consisting of balance, weight distribution across the foot, total weight applied to a foot, partial weight applied to the foot, foot movement, foot rotation, foot orientation, distance traveled, foot elevation, foot temperature, localized pressure on the foot, foot acceleration, foot speed, and dynamic load motion during foot movement.

In another embodiment, the data processing system is interfaced with an electronic game, such as a console game, computer game, or mobile game. In yet another embodiment, the sensor system is interfaced with a speaker, earbuds, headphones, or sound generation device to provide aural feedback to the subject. The sensor system is interfaced with a workforce-monitoring system for load on movement assessment. In another embodiment, the sensor system is interfaced with a biomechanical analysis system. In yet another embodiment, the sensor system is interfaced and time correlated with additional sensors at body locations other than the feet.

In one embodiment, the sensor system is configured to be used indoors. In another embodiment, the sensor system is configured to be used outdoors. In one embodiment, the method includes converting the two or more determined characteristics using a computing device to at least one of an output signal for moving an avatar in a virtual world or an output signal corresponding to a keyboard output signal. In yet another embodiment, the sensor system comprises one or more additional sensors selected from the group consisting of a global positioning system, an accelerometer, a gyroscope, an inertial navigation unit, a force sensor, a shear sensor, a pressure sensor, arrays of pressure sensors, a temperature sensor, a pulse sensor, and a blood pressure sensor. In another embodiment, in a reduced interconnect configuration, at least one of the sensor subsystems comprises a plurality of digital switches configured for pressure detection positioned adjacent to the bottom of the foot of the subject, wherein the at least one sensor subsystem is configured to use a binary weighted ladder digital-to-analog (D-A) conversion circuit. In another embodiment, the at least one sensor subsystem is configured to require an application of a force corresponding to a weight of the subject to activate the plurality of switches.

In another aspect, a force-sensitive substrate comprises a first force sensitive resistive (FSR) device having a first dynamic range and a second FSR device having a second dynamic range, where the first dynamic range is different from the second dynamic range. In one embodiment, the force-sensitive substrate the first FSR device and the second FSR device each have at least one of two FSR configurations: in a shunt mode FSR configuration, the FSR includes a semi-conductive material layer backed by a substrate, at least one spacer layer comprising a central hole, and a second layer comprising electrodes in an interdigitated pattern that drives a contact area between the two layers; and in a thru mode FSR configuration, the FSR device includes a semi-conductive material layer backed by a substrate, and a spacer layer that includes a central hole.

In another aspect, the force-sensitive substrate, the one of the first FSR device, and the second FSR device is configured to measure both an applied force and a position at a location, wherein the FSR device further comprises at least one of a linear potentiometer FSR configured to measure a position of the location with respect to one axis of translation and measure a force at the location, an XYZ digitizer FSR array configured to measure a position of the location with respect to two axes of translation and measure a force at the location, and an FSR matrix array configured to measure a position of the location with respect to three axes of translation and measure an applied force.

In one embodiment, a foot worn sensing device comprises the force-sensitive substrate wherein the first FSR device and the second FSR device of the force-sensitive substrate are hermetically sealed within a body of the force-sensitive substrate. The force-sensitive substrate is configured to maintain the first FSR device and the second FSR device hermetically sealed within the force-sensitive substrate when the force-sensitive substrate changes shape. In one embodiment, the at least one of the first dynamic range of the first FSR device and the second dynamic range of the second FSR device is optimized such that the difference between a minimum and a maximum output voltage of the at least one of the first dynamic range of the first FSR device and the second dynamic range of the second FSR device is about a factor of two. In another embodiment, the first dynamic range of the first FSR device or the second dynamic range of the second FSR device are modified by modifying at least one of the following characteristics of the FSR device: a spacer thickness of an FSR; a diameter of a central hole in a spacer layer of an FSR; a spacer Durometer hardness; a spacing between interdigitated conducting fingers of an FSR; a width of the interdigitated conducting fingers of an FSR; a thickness of the resistive layer; a thickness of a conducting finger substrate material; a Durometer hardness of a resistive layer or a Durometer hardness of a conducting finger substrate material; a sheet resistance of a resistive layer; an amount of dielectric dots; and a bias provided to an FSR to change a sensitivity of the FSR dynamically when using a transimpedance amplifier. In one embodiment, the first FSR device is configured to measure a force at a first predetermined anatomical location on a foot and the second FSR device is configured to measure a force at a second predetermined anatomical location on the foot. In another embodiment, the force-sensitive substrate comprises a third FSR device, wherein the first FSR device is configured to measure a force at the head of the first metatarsal, the second FSR device is configured to measure a force at the base of the fifth metatarsal and the third FSR device is configured to measure a force at about the calcaneus. In yet another embodiment, the force-sensitive substrate is sized and configured to match a shoe sole, an insole, or a pattern of anatomical locations. In another embodiment, the first FSR device and second FSR device are fabricated simultaneously in parallel and assembled as a single unit. In another embodiment, the first FSR device and the second FSR device are adhered to or embedded in the sole of the shoe. In one embodiment, the force-sensitive substrate is adhered to or embedded in an insole. In another embodiment, the force-sensitive substrate is adhered to or embedded in a piece of athletic equipment. In one embodiment, the athletic equipment is a helmet or protective padding. In one embodiment, the athletic equipment comprises one or more of the following: a ball, a bat, a golf club, a bicycle seat, a snow board, and a skateboard.

In one aspect, a system for measuring a subject's analog pulse waveform, comprises a plurality of force-sensitive resistors FSR positioned along a blood vessel, wherein each FSR is configured to measure a force exerted by the blood vessel, wherein the measured force of the blood vessel is indicative of a blood pressure characteristic, and wherein the subject's analog pulse waveform is determined by combining the measured blood pressure characteristics of each of the plurality of force-sensitive resistors. In one aspect, a method of biometric sensing includes identifying a user of a system by comparing the user's analog pulse waveform to a known analog pulse waveform.

In one embodiment, the system is also configured to determine a pedal pressure. In another embodiment, the system is part of a ring. In still another embodiment, the system is attached to a wrist. In another embodiment, the system is on a patch or a substrate that is flexible or stretchable.

In one aspect, a system for determining two or more characteristics of an activity performed by a subject, the system comprises two separate foot sensor subsystems, wherein each of the foot sensor subsystems is positioned adjacent to a separate foot of the subject, where each foot sensor subsystem comprises two or more sensor devices selected from the group consisting of a force sensor, an accelerometer, and a gyroscope, wherein each foot sensor subsystem is configured to output time-stamped measurement data. The output time-stamped measurement data includes the relative time that the measurement data was measured. The system further comprises a processing system separately located from at least one of the foot sensor subsystems. The two separate foot sensor subsystems and the processing system are configured to be in data communication one another. The processing system is further configured to: receive time-stamped activity data for each foot sensor subsystem, correlate the time-stamped activity data for each foot sensor subsystem to provide correlated activity data, and determine two or more characteristics of the activity of the subject using the correlated activity data.

DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Figure 1:
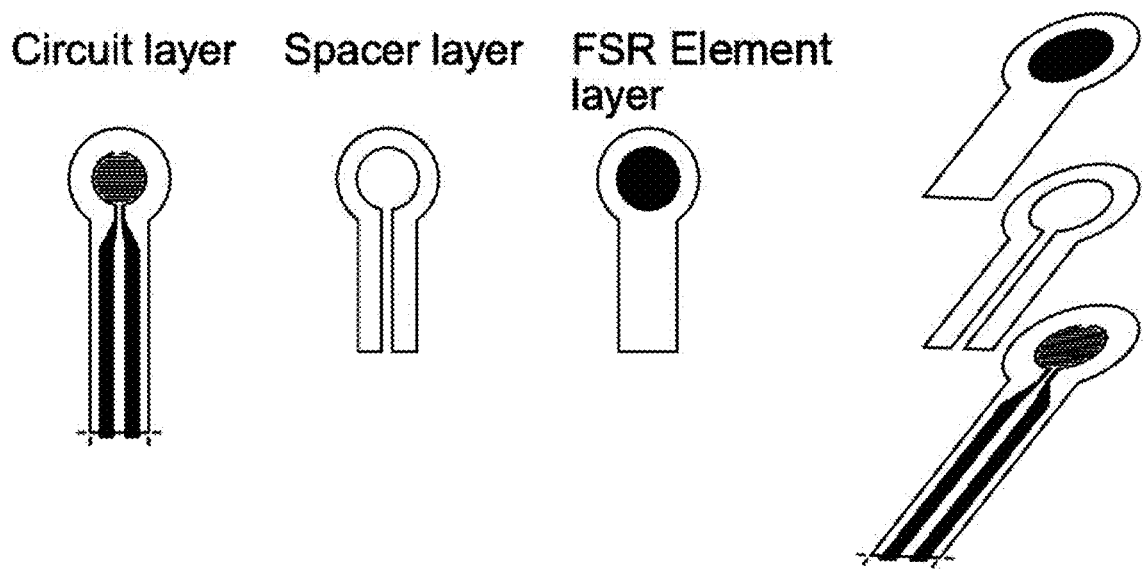
FIG. 1 illustrates a layered construction shunt mode FSR from the prior art.
Figure 2:
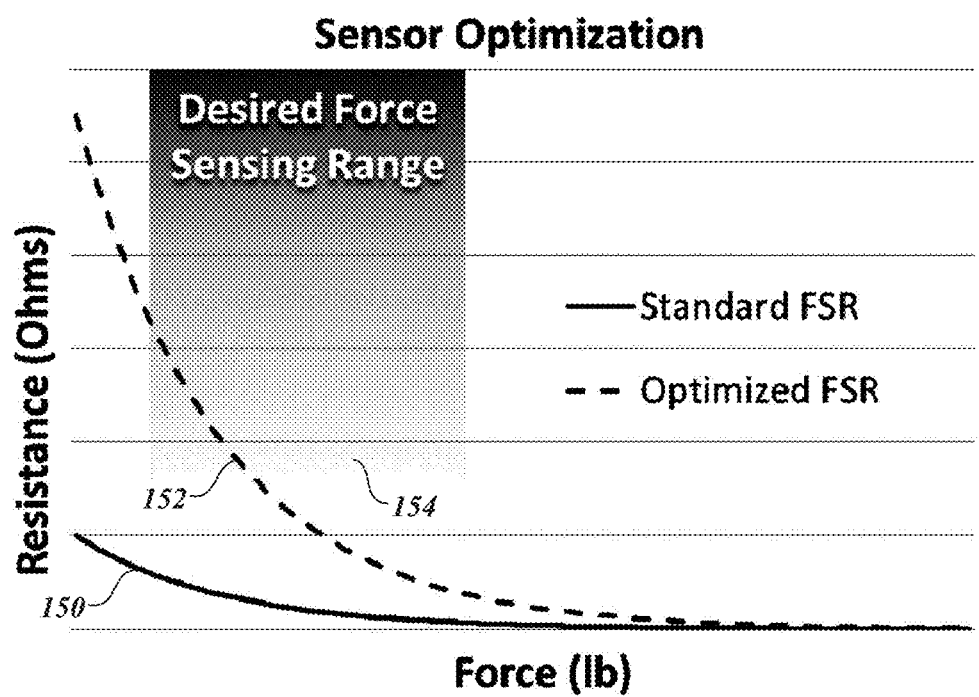
FIG. 2 is a plot of dynamic ranges of an FSR for a standard FSR and an optimized FSR in accordance with various embodiments of the present disclosure.

FIG. 2 shows a graph of force response curves for FSR optimization. A standard FSR response curve 150 and an optimized FSR response curve 152 are included in the graph. A desired force-sensing operating range 154 is also included in the graph of FIG. 2. A standard FSR with an operating range that is below the desired force-sensing operating range 154, such as is depicted in the standard FSR response curve 150, will essentially function as an on-off switch. An FSR with an operating range that is above the desired force-sensing operating range 154 will have an insufficient change in resistance for a given change in force. As shown by the optimized FSR response curve 152, when the dynamic range of an FSR is optimized for the expected force operating range, there is a measurably significant difference in resistance between forces within the expected force operating range.

In an FSR design there are particular FSR parameters that may be modified to alter the measurable dynamic and static force ranges of the device. In particular, the following parameters have great impact on altering a shunt mode FSR sensor for a given fixed actuator: spacer layer thickness, spacer layer inner diameter, spacer layer hardness (typically Durometer rating) of the spacer material, pitch or spacing of conductive interdigitating fingers, width of conductive interdigitating fingers, material used for semiconducting material and conducting fingers, thickness of polymer substrate of the semiconducting materials, hardness of conductive interdigitating fingers, sheet resistance of FSR material, presence and quantify of dielectric dots, spacing of dielectric dots, thickness of dielectric dots, and the presence or absence of a bias field. It is understood that modifying other FSR properties may be used to optimize the dynamic response according to currently known or later developed techniques. It is also understood that modifying an FSR or one of its properties may be accomplished by simply replacing one FSR with another FSR has particular properties or characteristics.

Figure 3:
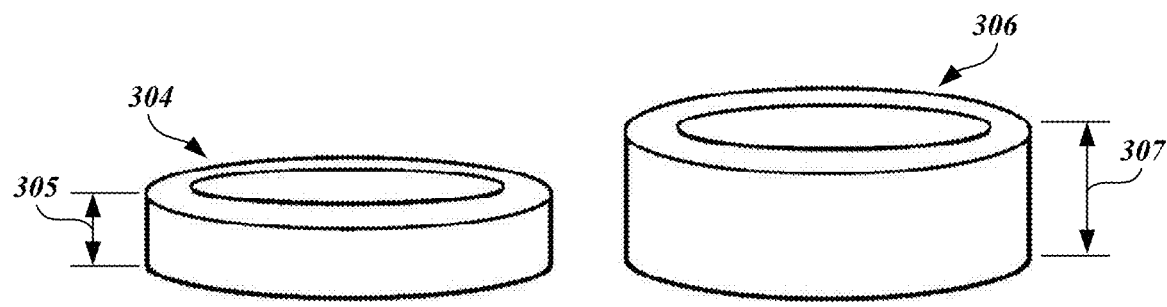
FIG. 3 illustrates a variation of FSR spacer thickness that may be used to modify the dynamic range of an FSR in accordance with various embodiments of the present disclosure.
Figure 4:
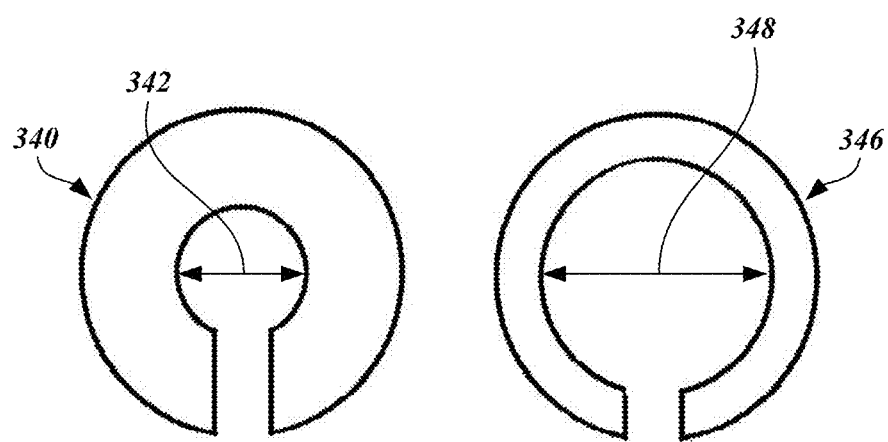
FIG. 4 illustrates a variation of spacer interior diameter between two FSRs used to optimize an FSR in accordance with various embodiments of the present disclosure.

FIGS. 3 and 4 show various FSR spacer layers. In particular, FIG. 3 shows a first spacer layer 304 having a spacer thickness 305 and a second spacer layer 306 having a spacer thickness 307. The magnitude of spacer thicknesses 305, 307 are different. An FSR that incorporates spacer layer 304 will have a different dynamic range property than an FSR that incorporates spacer layer 306 due to the different spacer thicknesses. A dynamic range may be optimized, as discussed in connection with FIG. 2, by using an FSR having either spacer thicknesses 305 and 307 depending on the magnitude of the force to be measured.

FIG. 4 depicts a third spacer layer 340 having an inner diameter 342 and a fourth spacer layer 346 having an inner diameter 348. The spacer layers 340 and 346 include an air gap, which may be used to relieve pressure. As shown, the inner diameters 342, 348 have different magnitudes. As discussed above in connection with FIG. 2, an FSR that uses the third spacer layer 340 will have a different dynamic range than an FSR that incorporates fourth spacer layer 346 based on the difference between inner diameters 342, 348. A dynamic range of an FSR may be optimized by using spacer layers of different inner diameters.

Figure 5:
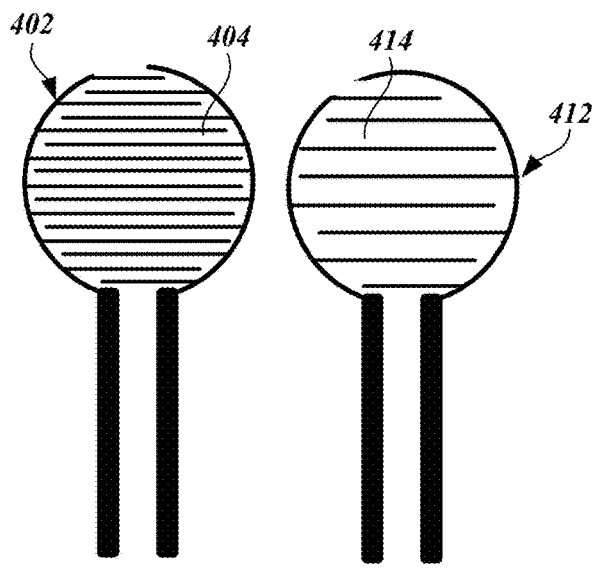
FIG. 5 illustrates a variation of pitch of conductive interdigitated fingers between two FSRs that may be used to optimize a dynamic range in accordance with various embodiment of the present disclosure.

FIG. 5 depicts a first set of conductive interdigitating fingers 402 having a first pitch 404 and a second set of conductive interdigitating fingers 412 having a second pitch 414 that is different from the first pitch 404. An FSR that uses the first pitch 404 will have a different dynamic range than an FSR having the second pitch 414. A dynamic range may be optimized by using an FSR having conductive interdigitating fingers of a particular pitch to shift the dynamic range up or down. Spacing between the interdigitating fingers may also be modified for an FSR in a similar way as pitch to modify the dynamic range of an FSR.

Figure 6:
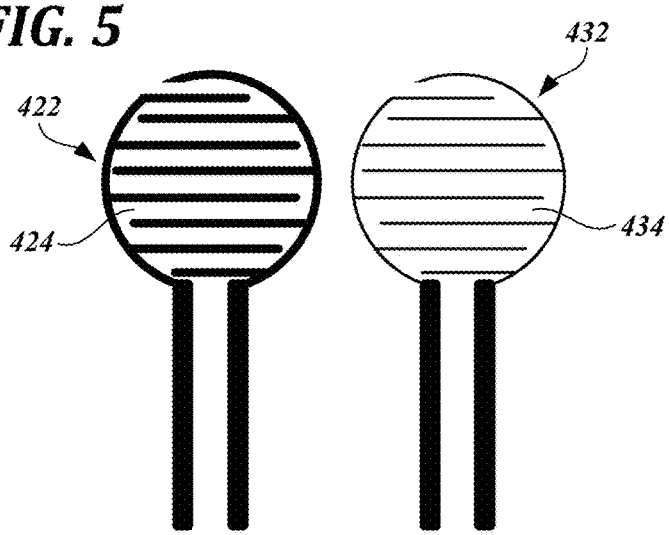
FIG. 6 illustrates a variation of trace width between conducting interdigitated fingers of two FSRs that may be used to optimize a dynamic range of an FSR in accordance with various embodiments of the present disclosure.

FIG. 6 depicts a third set of conductive interdigitating fingers 422 having a first finger width 424 and a fourth set of conductive interdigitating fingers 432 having a second finger width 434. An FSR that uses the second finger width 434 will have a different dynamic range than an FSR that incorporates first finger width 424. Some embodiments may include FSRs with modified dynamic ranges based on utilizing a set of conductive interdigitating fingers having different finger widths.

Figure 7:
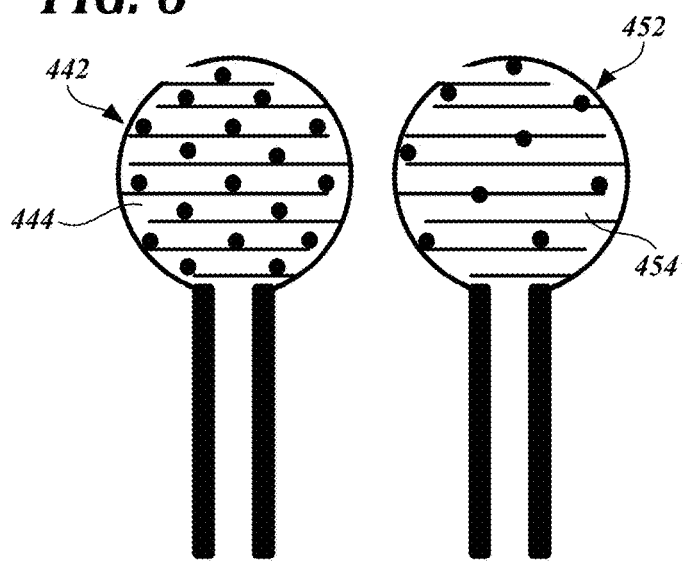
FIG. 7 illustrates a variation in spacing and quantity of dielectric dots between two FSRs in accordance with various embodiments of the present disclosure.

FIG. 7 depicts a fifth set of conductive interdigitating fingers 442 having a first thickness and quantity of dielectric dots 444, and a sixth set of conductive interdigitating fingers 452 and second conductive interdigitating fingers 454 having a second first thickness and quantity of dielectric dots 454. A dynamic range of an FSR may be modified by using different thicknesses and quantities of dielectric dots such as first and second thicknesses and quantities of dielectric dots 444, 454.

Multiple FSRs can be incorporated into a single printed device, particularly in matrix or array form. Specifically, one and two dimensional arrays of FSRs may be configured to measure position of the force in one or two dimensions while simultaneously measuring the force itself to form respectively linear potentiometers and XYZ digitizer pads as described in U.S. Pat. No. 4,739,299, issued to Eventoff et al. ("Eventoff II").

Figure 8:
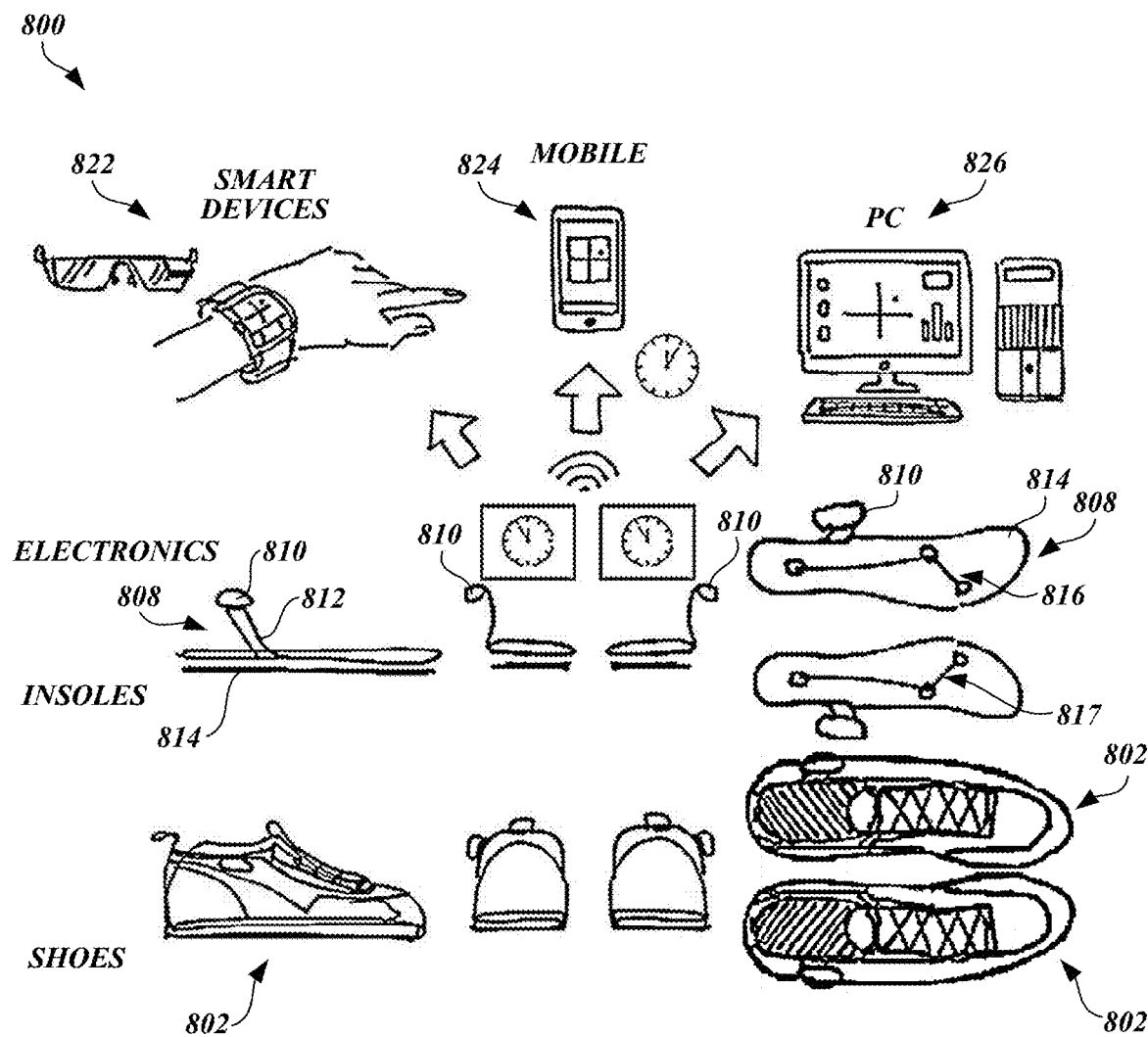
FIG. 8 illustrates using a wearable footwear system to determine the projection of center of gravity (POCG) or balance in accordance with various embodiments of the present disclosure.

A wearable footwear sensor system 800 is shown in FIG. 8. Wearable footwear sensor system 800 includes footwear 802, a foot sensor subsystem 808, a master device, such as a smart watch 822, mobile electronic device 824, or a personal computer 826. The foot sensor subsystem 808 includes sensor-enabled insoles or insert 814, footwear electronics 810 that may be disposed within or on the footwear 802, and interconnects 812 that connect the footwear electronics 810 to sensing devices 816, 817 in the sensor-enabled insoles or insert 814. Thus, footwear electronics 810 are hard wired to sensing devices 816, 817. Sensing devices 816, 817 may be included within or on the sensor-enabled insoles or insertable device 814. Sensing devices 816, 817 may include FSRs or other types of sensors such as piezoelectric sensors.

In some embodiments, the footwear electronics 810 include or may be communicatively coupled to additional sensors, such as one or more accelerometers. As discussed in more detail below, the footwear electronics 810 and the master device are configured to communicate with one another via suitable communication modules. In some embodiments, the Bluetooth standard is used for wireless communication between footwear electronics 810 and one or more of the master devices. However, it is understood that other types of wireless communication standards or protocols and associated hardware, currently known or later developed, may be used to provide wireless communication between the footwear electronics 810 and the master device. In some embodiments, the master device is configured to provide clock synchronization for the footwear electronics 810. The master device may include, for example, a watch, heads-up display, glasses display, smartphone, personal digital assistant, computer (tablet, laptop, desktop, etc.), MP3 or MP4 player, television, other microprocessor-containing device, other display containing device or other similar device.

In one aspect, a method of determining two or more characteristics of an activity performed by a subject comprises providing a sensor system, such as the wearable footwear sensor system shown in FIG. 8. The sensor system includes two separate foot sensor subsystems 808, each comprising two or more sensor devices selected from the group consisting of a force sensor, an accelerometer, and a gyroscope, wherein each foot sensor subsystem is configured to generate time-stamped device data that includes a relative time that the device data was generated, wherein each of the foot sensor subsystems is configured to be coupled to a separate foot of the subject. The provided sensor system also includes a data processor system in communication with both of the foot sensor subsystems and located separate from at least one of the foot sensor subsystems. The data processor system includes any electronic device such as the master device discussed in connection with FIG. 8. The data processor system may also include more than one electronic device that may be in communication with one another. The method also comprises generating time-stamped activity data during the activity for each foot sensor subsystem based on the time-stamped device data output, communicating the time-stamped activity data for each foot sensor subsystem to the data processor system, correlating the time-stamped activity data from each foot sensor subsystem to provide correlated activity data using the data processor system, and determining two or more characteristics of the activity of the subject using the correlated activity data using the data processor system.

Figure 11:
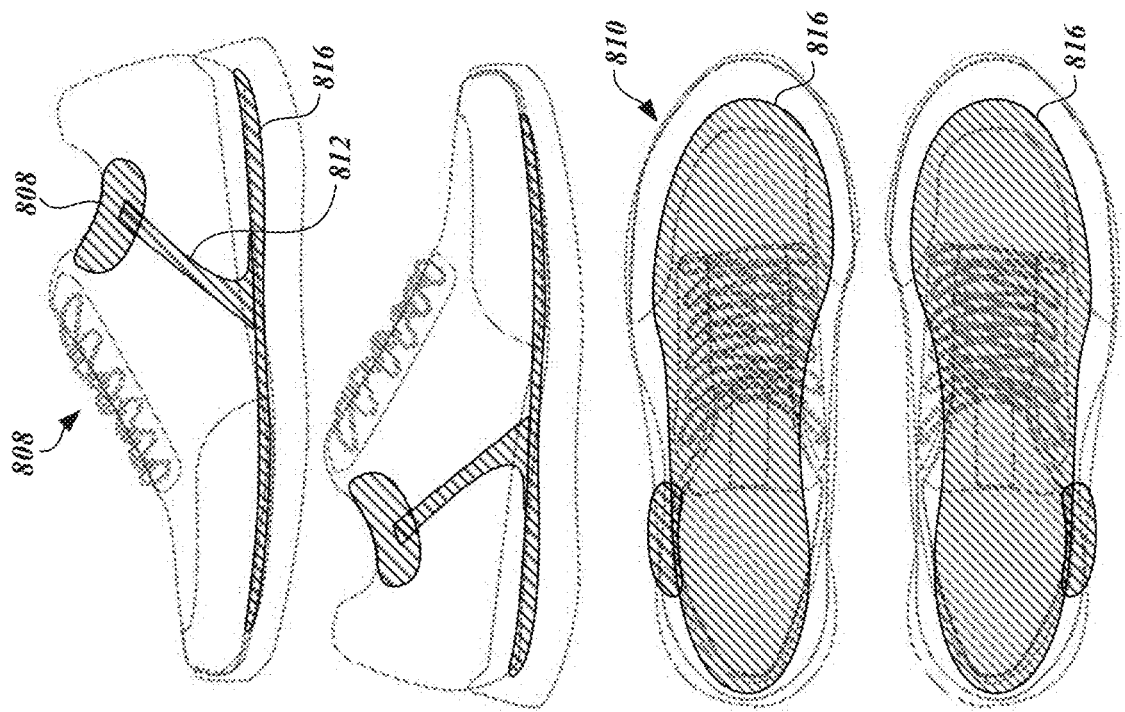
FIG. 11 illustrates a foot sensor subsystem including sensor-enabled insoles and inserts in accordance with various embodiments of the present disclosure.
Figure 11:
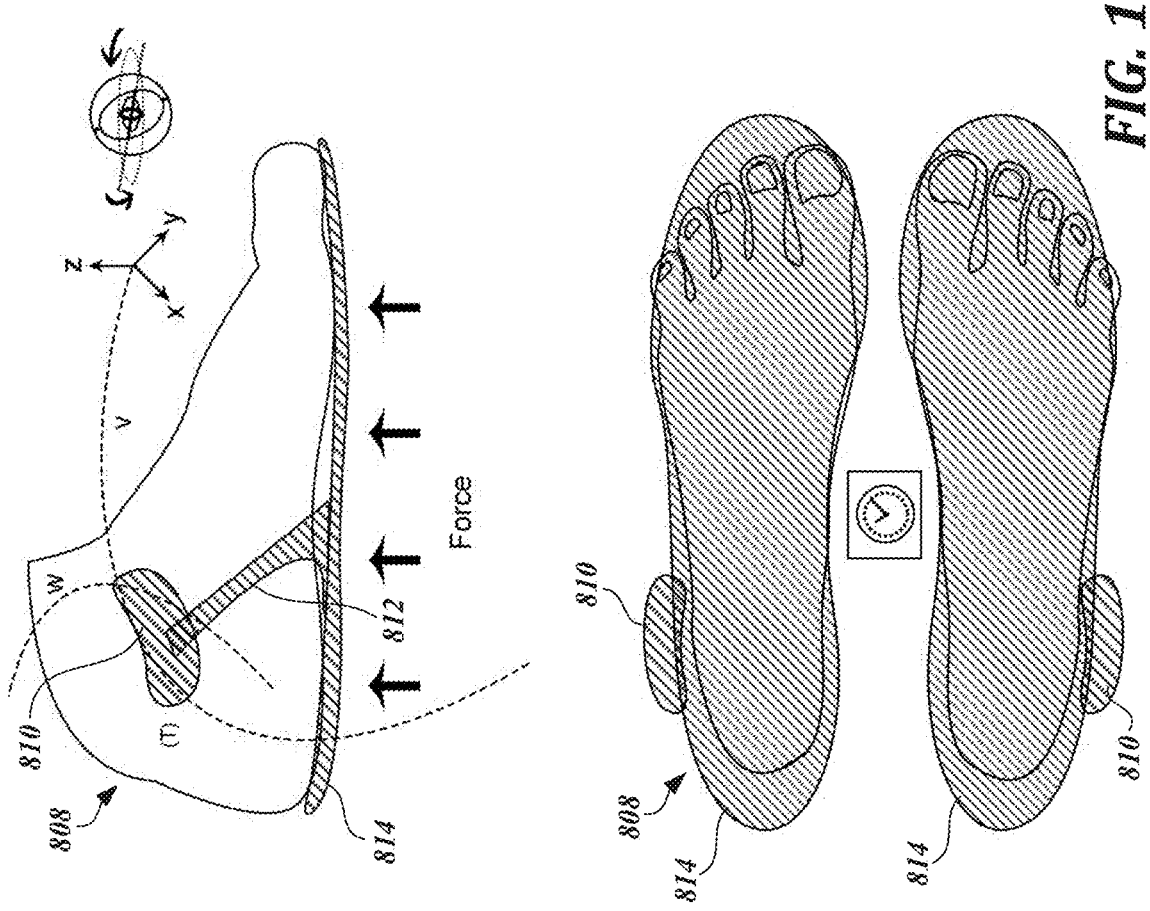
Figure 20:
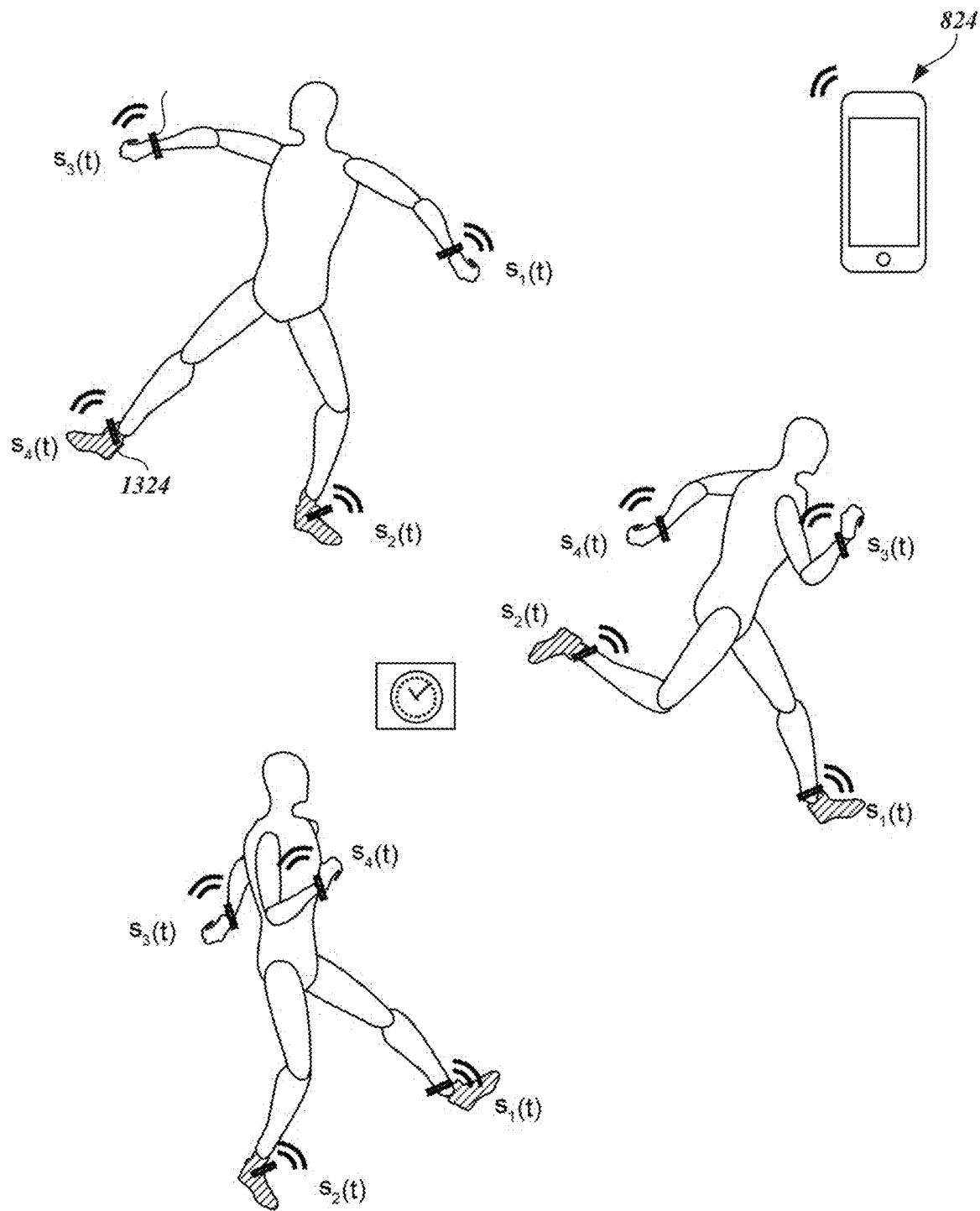
FIG. 20 illustrates a system that including foot sensor subsystems as well as other sensors located at body parts other than a foot.
Figure 24:
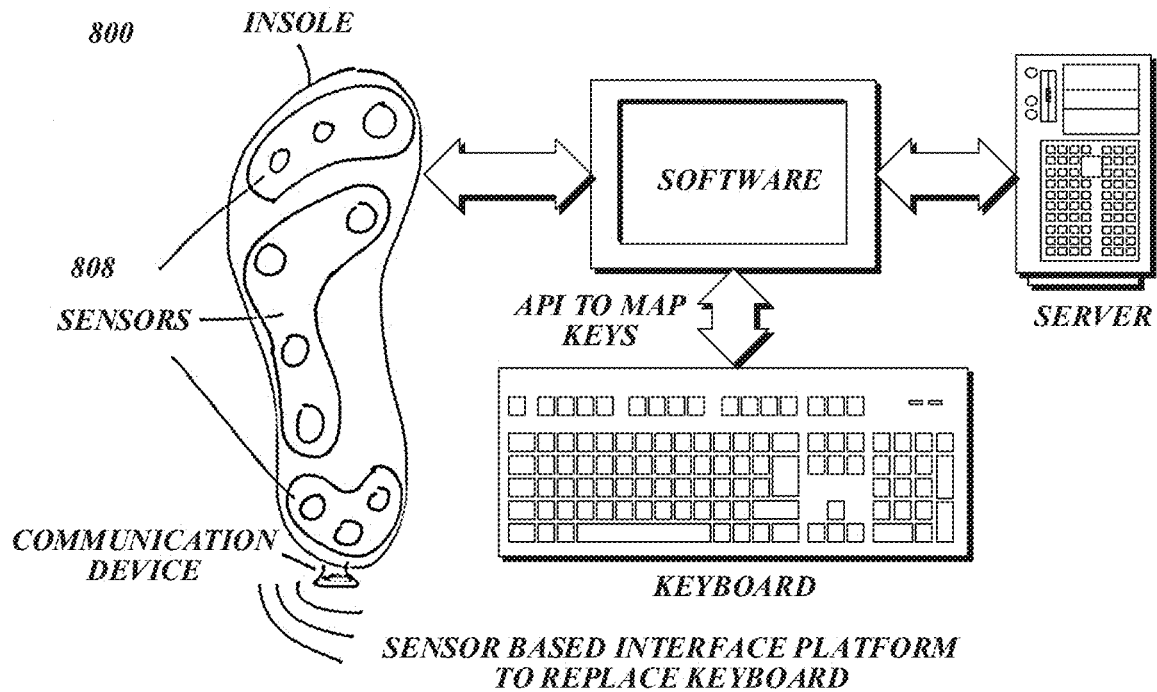
FIG. 24 is a pictorial representation of a foot sensor subsystem used of a wearable sensor footwear system configured as a I/O device controller in accordance with an embodiment of the present disclosure.
Figure 25:
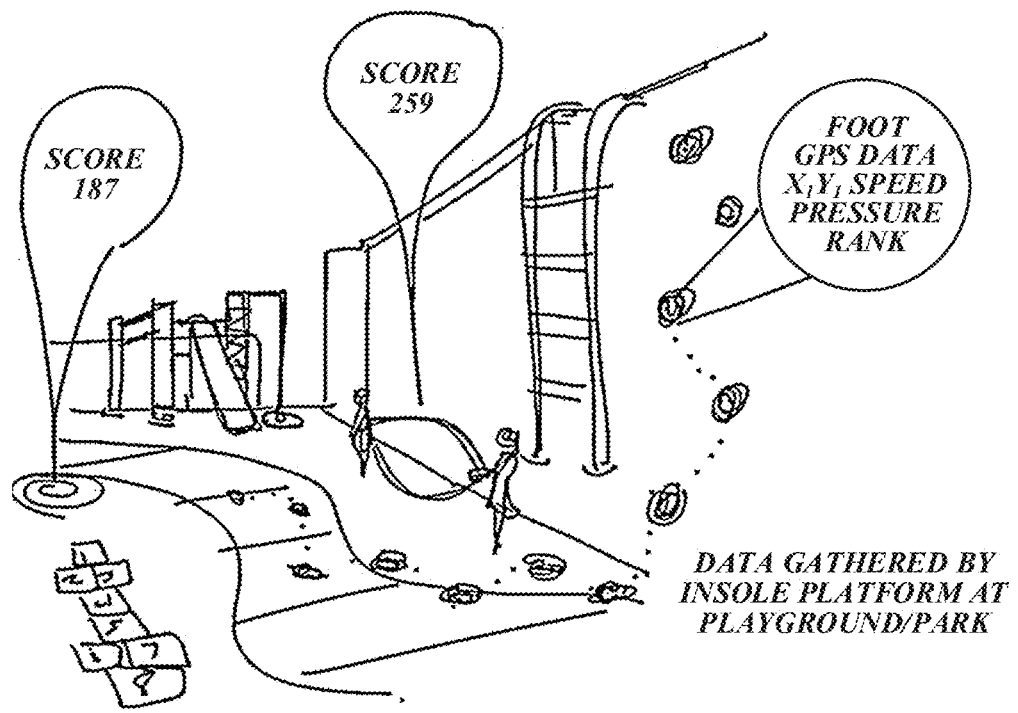
FIG. 25 is a pictorial representation an outdoor gaming application that may be use embodiments of the present disclosure.

In one aspect, each foot sensor subsystems further comprises a clock for deriving the time stamps of individual devices, wherein each clock is synchronized by communication with a master device. The data processor system may include the master device. In another aspect, the data processor system includes a display device. In still another aspect, the two or more characteristics determined by the sensor system are selected from the group consisting of balance, weight distribution across the foot, total weight applied to a foot, partial weight applied to the foot, foot movement, foot rotation, foot orientation, distance traveled, foot elevation, foot temperature, localized pressure on the foot, foot acceleration, foot speed, and dynamic load motion during foot movement. As discussed below in more detail, in another aspect, the data processing system is interfaced with an electronic game, such as a console game, computer game, or mobile game. As discussed below in more detail, in another aspect, the sensor system is interfaced with a speaker, earbuds, headphones, or sound generation device to provide aural feedback to the subject. In another aspect, the sensor system is interfaced with a workforce-monitoring system for load on movement assessment. In still another aspect, discussed in more detail below, the sensor system is interfaced with a biomechanical analysis system. In still another aspect, discussed below in more detail, the sensor system is interfaced and time correlated with additional sensors at body locations other than the feet such as shown in FIG. 20. In still another aspect, the sensor system is configured to be used indoors. In still another aspect, the sensor system is configured to be used outdoors. For example, the electronics may be covered and/or the sensor devices may be partially or completely hermetically sealed such as is shown in FIG. 11. In another aspect, the method further comprises converting the two or more determined characteristics using a computing device to at least one of an output signal for moving an avatar in a virtual world such as is depicted in FIG. 25, or an output signal corresponding to a keyboard output signal such as is shown in FIG. 24.

In another aspect, the sensor system, such as sensor system 800, further comprises one or more additional sensors selected from the group consisting of a global positioning system, an accelerometer, a gyroscope, an inertial navigation unit, a force sensor, a shear sensor, a pressure sensor, arrays of pressure sensors, a temperature sensors, a pulse sensors, and a blood pressure sensor. In another aspect, in a reduced interconnect configuration, at least one of the sensor subsystems comprises a plurality of digital switches configured for pressure detection positioned adjacent to the bottom of the foot of the subject, wherein the at least one sensor subsystem is configured to use a binary weighted ladder digital-to-analog (D-A) conversion circuit. In another aspect, the at least one sensor subsystem is configured to require an application of a force corresponding to a weight of the subject to activate the plurality of switches.

The Bluetooth protocol does not inherently provide such synchronization. Most of the state-of-the-art body tracking and fitness devices use devices placed on arms. The coordinate system used to describe body kinetics and kinematics for arm-based sensors is ill-defined by being placed at the sensing capture point, i.e., sensor at the wrist. In embodiments described in the present disclosure, the body coordinate system is localized at the base of the human foot where data capture is occurring. This placement system reduces errors on calculations and corrections between coordinate systems to describe human body movement.

Figure 9:
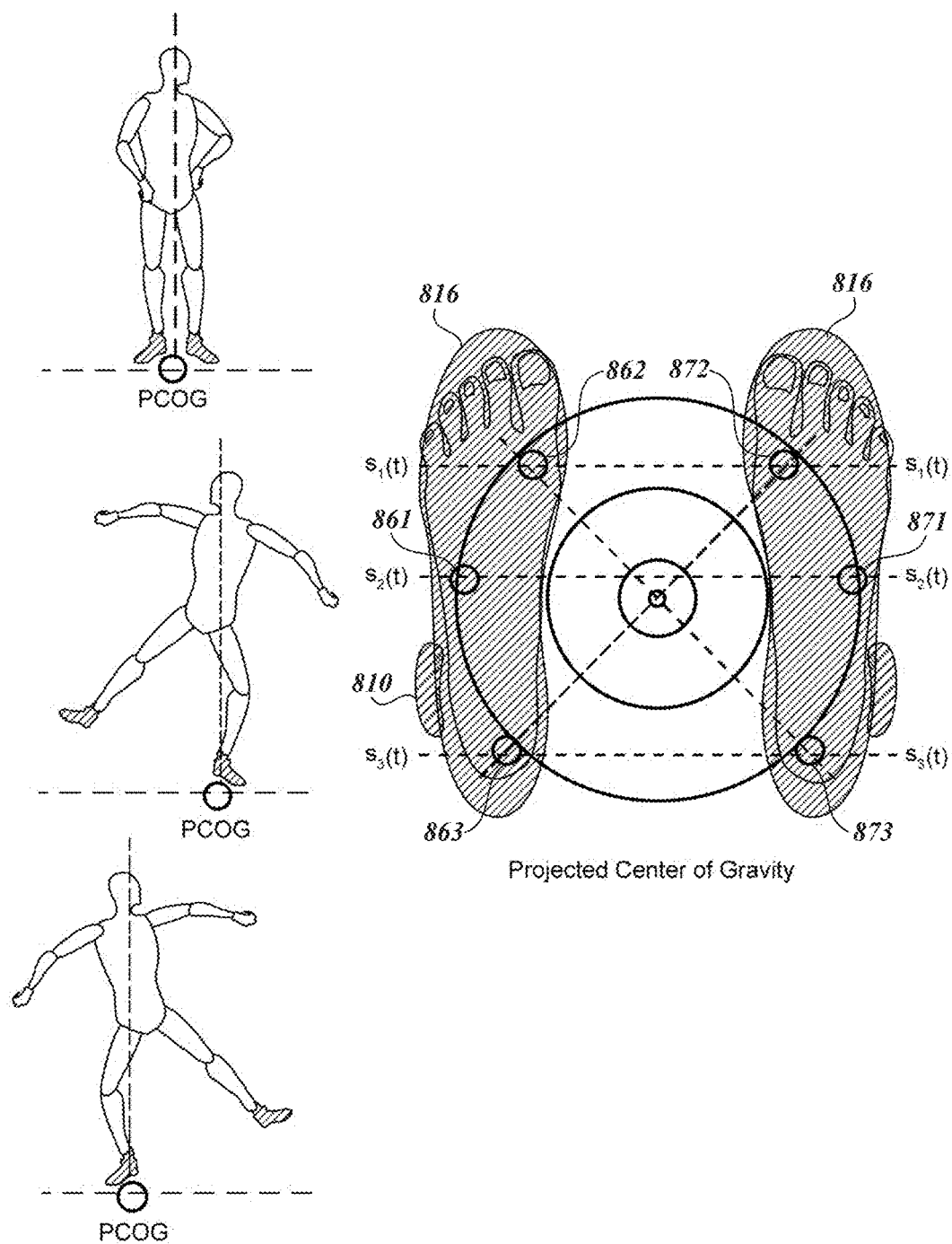
FIG. 9 illustrates foot-based sensors to determine the projection of center of gravity (POCG) or balance.

FIG. 9 depicts how shoe-based sensors may determine the projection of center of gravity (POCG). In particular, by using measurements from sensors 861, 862, 863, 871, 872, and 873 on a still position, a vector sum of those spatial forces is computed and placed on the centroid of a convex polygon region defined by each sensor position. By taking an initial measurement on a still position, a baseline for the POCG is defined because of the symmetry of the polygon along the axis of the feet, thus the length separation between both feet is not required. Next, any change in force on each sensor due to movement or weight shift is used to recalculate the vector sum of the spatial forces and the values are used to change the position of POCG on the baseline polygon using triangulation calculations for example.

Wearable footwear sensing system 800 may be used to provide two or more characteristics of the foot, such as, but not limited to, a foot pressure at various localized anatomical locations on each foot, weight distribution across a foot, total weight applied to a foot, partial weight applied to a foot, foot shear force, balance, movement of the POCG, movement of the subject body, orientation of a foot, elevation of a foot, motion and speed of a foot, rotation of a foot, acceleration of a foot, distance traveled by a subject, foot temperature, dynamic load motion during foot movement, and differences in these characteristics among feet of multiple subjects.

Figure 10:
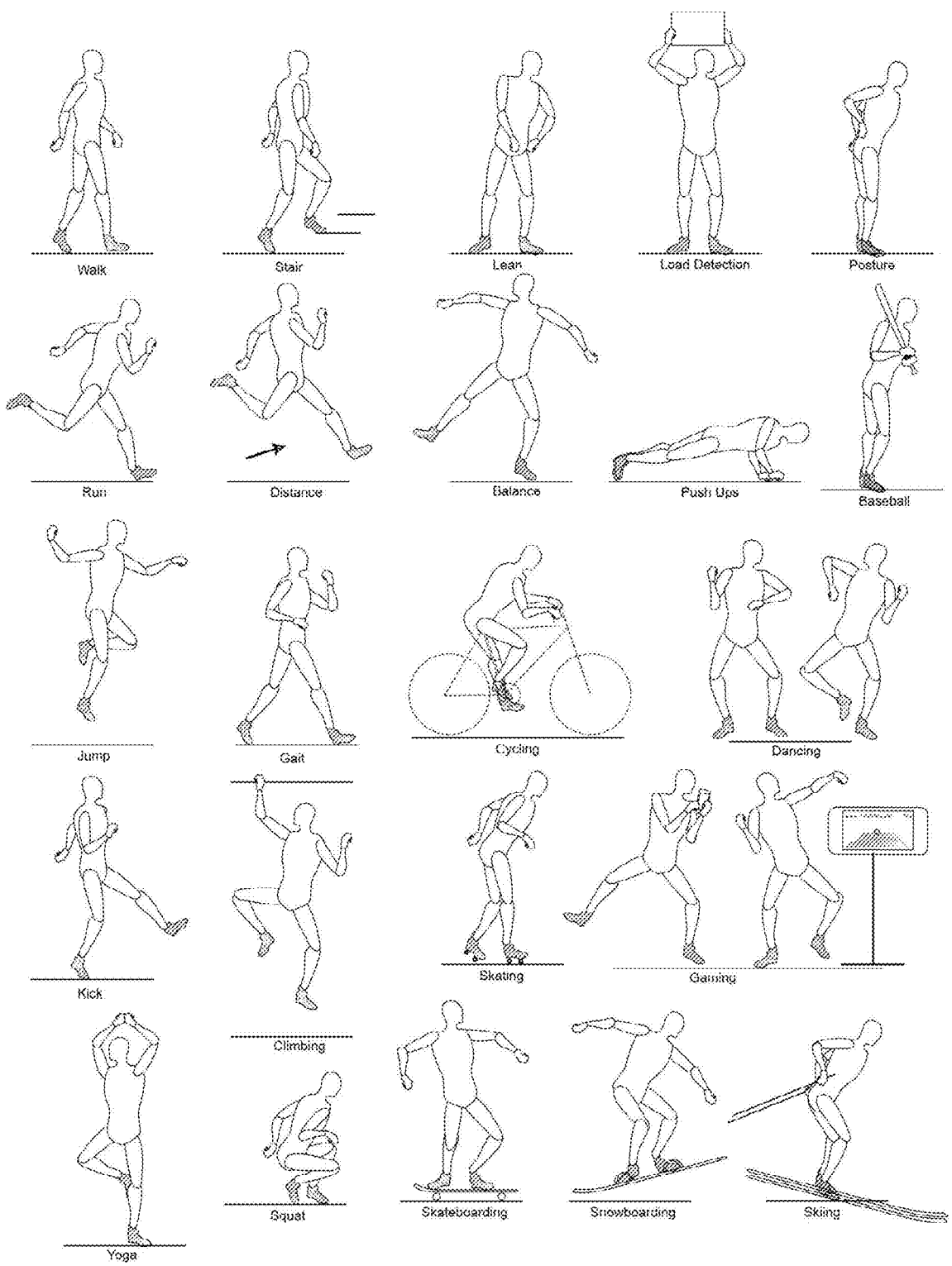
FIG. 10 illustrates foot characteristics that may be determined using the system disclosed in FIG. 8.
Figure 12:
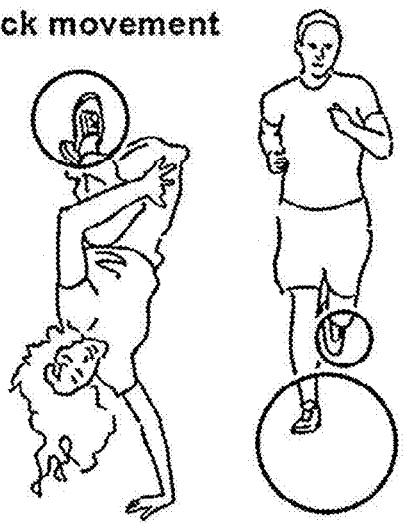
FIG. 12 is a pictorial representation of activities that may be used with various embodiments of the present disclosure.
Figure 12:
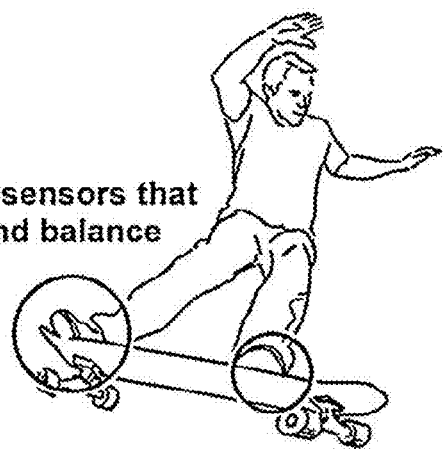

FIG. 10 shows characteristics of activities that may be determined using embodiments of the present disclosure. In some embodiments, characteristics of the activities shown in FIG. 10 may be determined by wearable footwear sensor system 800 using two different types of sensors: sensors for determining force and pressure on the bottom of the foot; and sensors for measuring motion and position. As mentioned above, the latter may be positioned adjacent to the footwear electronics 810. FIG. 12 shows these conceptually in activities. Both feet of a subject are monitored to determine balance.

Foot sensor subsystem 808 may include various sensor technologies using digital (e.g., switches) and/or analog circuits. Digital sensing technologies are simpler, but generally digital sensing technologies allow only a single on-off input from each switch. By contrast, analog sensors allow continuously variable inputs, which may be better suited for use with games where measuring accelerations, jumping with different heights and lengths, swings and punches of various strengths, as well to detect physical activities such as steps, walking, running, etc. Analog technologies may be better for measuring steady state force inputs or dynamic acceleration inputs of a subject.

Force/Pressure Sensors

Sensor technologies for measuring force and/or pressure include, but are not limited to, the following steady state and dynamic sensors: thin electrical switches that respond to perpendicular pressure (digital) FSRs, elastic-conducting composites, force sensitive capacitors (steady state), piezoelectric materials and devices (dynamic), piezoelectric ceramics, piezoelectric composites, piezoelectric single crystals, piezoelectric epitaxial films, piezoelectric polymers, polyvinylidene fluoride (PVDF), co-polymers such as poly(vinylidene fluoride-trifluoroethylene) (P(VDF-TrFE)), magnetic sensors where a magnetic field is sensed by various means (steady state or dynamic), mechanical sensors where the field from a magnet varies compression of an air gap, magnetostrictive sensors where a force is converted to a magnetic field, force sensing optical materials and devices such as Fiber Bragg Gratings (FBGs), which are capable of modifying a signal in an optical fiber or other optical device (steady state or dynamic), or any other technology capable of measuring a force and converting it into an electric signal. These sensors may be biased to require a threshold weight, such as of the subject, in order to be activated.

In one aspect, a force-sensitive substrate comprises a first force sensitive resistive device having a first dynamic range and a second FSR device having a second dynamic range, wherein the first dynamic range is different from the second dynamic range. As discussed in connection with FIG. 2, the dynamic range may be optimized based on a desired force sensing range. The force-sensitive substrate, for example, may include the inserts or sensor-enabled insoles 814 of FIG. 8 or various other inserts/insoles shown in FIGS. 11 and 14. In one aspect, the force-sensitive substrate, in which the first FSR device and the second FSR device each have at least one of two FSR configurations: (a) in a shunt mode FSR configuration, the FSR includes a semi-conductive material layer backed by a substrate, at least one spacer layer comprising a central hole, and a second layer comprising electrodes in an interdigitated pattern that drive a contact area between the two layers; and (b) in a thru mode FSR configuration, the FSR device includes a semi-conductive material layer backed by a substrate, and a spacer layer comprising a central hole. In one aspect, one of the first FSR device and the second FSR device is configured to measure both an applied force and a position at a location, wherein the FSR device further comprises at least one of (a) a linear potentiometer FSR configured to measure a position of the location with respect to one axis of translation and measure a force at the location; (b) an XYZ digitizer FSR array configured to measure a position of the location with respect to two axes of translation and measure a force at the location; and (c) an FSR matrix array configured to measure a position of the location with respect to three axes of translation and measure an applied force.

In one aspect, a foot worn sensing device comprises the force-sensitive substrate, where the first FSR device and the second FSR device of the force-sensitive substrate are hermetically sealed within a body of the force-sensitive substrate, and the force-sensitive substrate is configured to maintain the first FSR device and the second FSR device hermetically sealed within the force-sensitive substrate when the force-sensitive substrate changes shape. In another aspect, at least one of the first dynamic range of the first FSR device and the second dynamic range of the second FSR device is optimized, such as shown in FIG. 2, such that the difference between a minimum and a maximum output voltage of the at least one of the first dynamic range of the first FSR device and the second dynamic range of the second FSR device is about a factor of two.

In another aspect, as discussed in connection with FIGS. 2-7, the first dynamic range of the first FSR device or the second dynamic range of the second FSR device is modified by modifying at least one of the following characteristics of the FSR device: a spacer thickness of an FSR; a diameter of a central hole in a spacer layer of an FSR; a spacer Durometer hardness; a spacing between interdigitated conducting fingers of an FSR; a width of the interdigitated conducting fingers of an FSR; a thickness of the resistive layer; a thickness of a conducting finger substrate material; a Durometer hardness of a resistive layer or a Durometer hardness of a conducting finger substrate material; a sheet resistance of a resistive layer; an amount of dielectric dots; and a bias provided to an FSR to change a sensitivity of the FSR dynamically when using a transimpedance amplifier. In another aspect, the first FSR device is configured to measure a force at a first predetermined anatomical location on a foot and the second FSR devices is configured to a force at a second predetermined anatomical location on the foot such as is shown and discussed in connection with FIGS. 8, 9, 13, and 14. In another aspect, the force-sensitive substrate further comprises a third FSR device, wherein the first FSR device is configured to measure a force at the head of the first metatarsal, the second FSR device is configured to measure a force at the base of the fifth metatarsal and the third FSR device is configured to measure a force at about the calcaneus. In another aspect, the force-sensitive substrate is sized and configured to match a shoe sole, an insole, or a pattern of anatomical locations. In another aspect, the first FSR device and the second FSR device are fabricated simultaneously in parallel and assembled as a single unit. In another aspect, the first FSR device and the second FSR device are adhered to or embedded in the sole of the shoe. In another aspect, the force-sensitive substrate is adhered to or embedded in an insole. In another aspect, the force-sensitive substrate is adhered to or embedded in a piece of athletic equipment such as is shown and discussed in connection with FIGS. 22, 23, and 26. In particular, the athletic equipment may be one or more of the following: a ball, a bat, a golf club, a bicycle seat, a snow board, and a skateboard.

FSRs are used in many of the technological descriptions because preliminary studies have found that FSRs are uniquely suited to in-shoe steady state sensors. It should be understood that other types of force sensors currently known or later developed may be used in the embodiments disclosed herein. Also, it should be understood that the independent optimization of multiple FSRs on a common platform of the present disclosure is directly applicable to the inventions of this disclosure multiple anatomical sensor locations may be optimized for the performance of the FSR located thereon.

Figure 13:
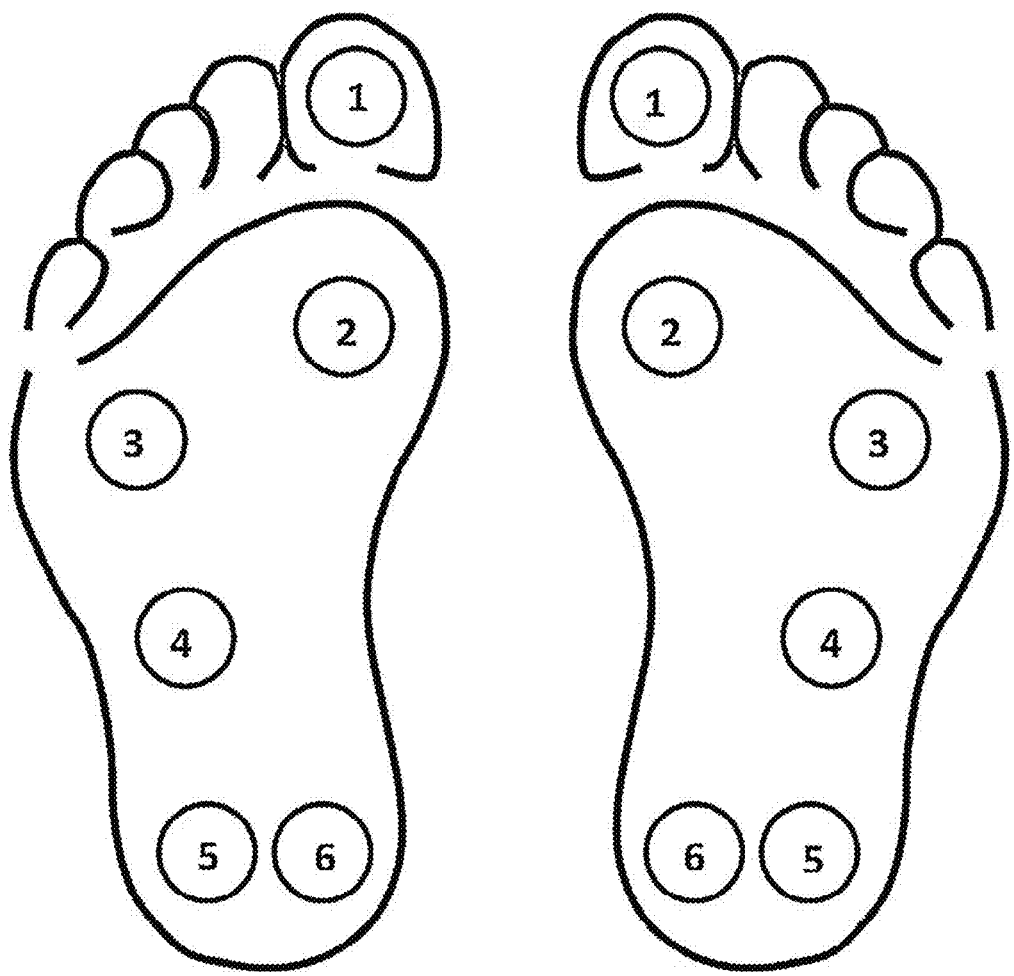
FIG. 13 illustrates foot locations where force-sensitive resistors may be positioned.

Six different locations in which the actuation of sensors is useful for gaming interactions and body movement are illustrated in FIG. 13. The sensor locations shown in FIG. 13 encompass some of the major pressure points on the foot that allocate the user to control a game based upon standard body movements, including premeditated motions, gait, and balance. In some embodiments, a sensor is positioned adjacent to each of the sites 1-6 illustrated in FIG. 13. When actuated, each sensor, or a collection of sensors, can act as a specific control for a game in either a digital or analog mode.

In some embodiments, a sensor is positioned at the outer calcaneus and another sensor positioned at the inner calcaneus, which may offer a unique capability of sensing balance. However, the outer and inner calcaneus (heel region) sensors can be combined into a single sensor located directly below the calcaneus bone. In some embodiments, a sensor may be positioned directly under the head of the fifth metatarsal bone. In some embodiments, a sensor may be positioned such that it overlaps both the heads of the fourth (not shown) metatarsal bone and the fifth metatarsal bones.

In some embodiments, sensors are configured to sense in general locations, reducing the need for a specific set-up exactly tailored to a particular foot or to a particular shoe size. A collection of sizes such as small, medium, and large would produce a platform to fit most feet. In some embodiments, a men's small is suitable for use with feet and shoes having a shoe size in the range of size 6-8, a men's medium is suitable for use with feet and shoe sizes ranging from 9-11, and a men's large would be suitable for use with a shoe sizes ranging from sizes 12-14.

To further compatibility with various types and styles of shoes, the electronic packaging of the sensors can be fabricated individually, collectively or integrated into a shoe insert, commonly referred to as an insole or sock liner. Inserts may be manufactured out of silicone rubbers and foams due to their desirable Durometer ratings, water repellency, and desirable antimicrobial properties. Insoles are commonly removed or replaced in shoes to produce a better fit or promote proper biomechanics. This broadens the ease of use of the system by providing a generic platform that can easily be integrated into and be compatible with a wide range of footwear.

Figure 14:
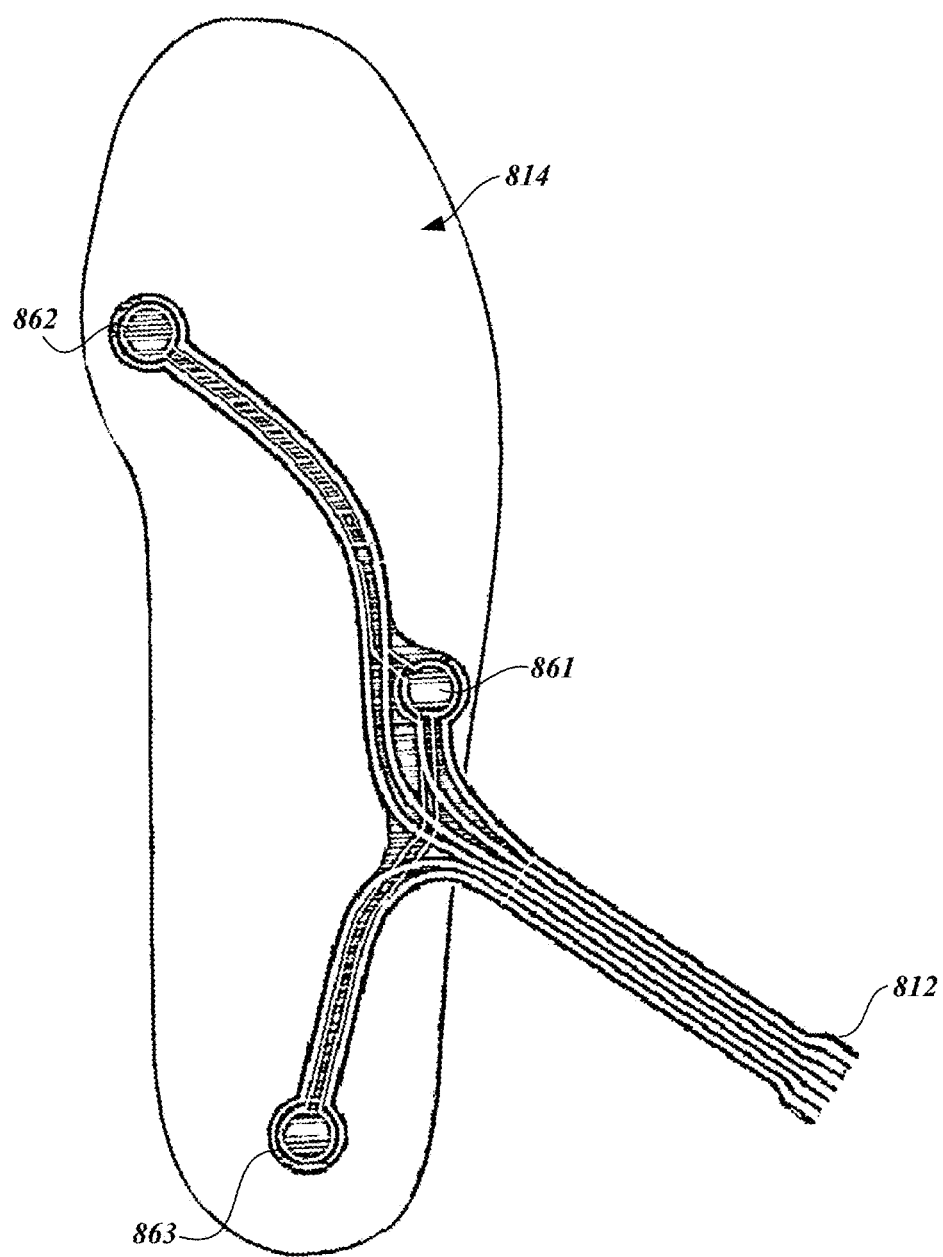
FIG. 14 illustrates sensor enables insoles suitable for use with various embodiments of the present disclosure.

A set of FSRs may be printed simultaneously in parallel on a common set of substrates and assembled as a single unit shaped to fit in a shoe can provide improved durability and comfort for a user. An example insole 814 includes a system of interconnects 812 and sensors 861, 862, and 863 are shown in FIG. 14. The insole 814 has a shape that matches the inside of a shoe. This shape and assembly process may provide numerous benefits. In particular, the sensor enable insoles 814 shown in FIG. 14 help minimize irritation of a subject because the sensor enable insoles 814 encompass the entirety of the bearing surface on the foot. In addition, the embodiment shown in FIG. 14 would have reduced edge effects that would change the sensor output compared to an un-instrumented shoe. The shape of the sensor enable insoles 814 is also sized and configured to match the inside of a shoe, which helps to reduce movement within the shoe and enhance stability.

In some embodiments, a shaped set of sensors is deposited (e.g., printed) or laminated inside the shoe itself or to the insole. In such embodiments, the interconnects 812 and/or sensors 816 or 817 are supported by a substrate material of the sensor enable insoles 814, which helps to prevent damage. If sensor enable insoles 814 are laminated or embedded into the footwear 802, the interconnects 812 could be even further supported by the footwear 802. The piece could be shaped to fit exactly either the sole of the shoe or the flat portion of the insole to prevent any effects from three dimensional contouring.

In some embodiments, it is desirable to limit the humidity and heat effects to the sensors, such as first, second, and third FSRs 861, 862, and 863. The sensor enable insoles 814 could be made semi-hermetic by covering, for example, any venting openings leading to the air gap of each FSR sensor of the sensor enable insoles 814 with material permeable to air, but not water or by the simple expedient of having the vent gap be long enough to limit back flow of air while being vented to a protected location within the sensor enable insoles 814. The protected location may be, for example, a heel counter. In some embodiments, the design could be made fully hermetic by creating air expansion spaces within the sensor enable insoles 814 where there is no foot pressure and sealing the sensors, such as FSRs, within the sensor enable insoles 814. Some embodiments of sensor enable insoles 814 are made temperature insensitive by utilizing temperature insensitive semiconducting resistor materials.

In some embodiments, the individual sensors are optimized or otherwise configured to have a dynamic range matched to an anatomical location based on an expected, average, and/or peak forces for the anatomical location of the sensor. The expected, average, and peak forces for the anatomical location may be based on a weight of the subject or the activity being performed by the subject. As discussed above in connection to FIGS. 3, 4, and 6, three adjustments to an FSR to modify or adjust the dynamic range are the pitch (spacing) between interdigitated fingers, spacer thickness, and spacer opening. As discussed above in connection with FIG. 6, increasing the pitch between the fingers can reduce the conductivity between fingers, which modifies the dynamic range. Another parameter that may be modified is spacer thickness. With increasing spacer thickness, a greater force is required to bring the FSR and interdigitating fingers into contact with one another. Spacer thickness can affect sensitivity of an FSR, as too thick a spacer could prevent substantial conduction between the FSR and conductive fingers from occurring for a range of forces. Another FSR parameter that may be modified to adjust the dynamic of the FSR is the diameter of the spacer opening. If the spacer opening diameter is too large, the sensor will reach its minimum resistance when actuated by relatively low forces. If the spacer opening diameter is too small for the forces exerted on the sensor, no conduction will be made. In some embodiments, an optimal opening corresponds to when there is relatively small conduction while the subject is standing still.

In other embodiments, an FSR with a particular desired dynamic range adding or removing dielectric dots, changing sensor thickness, or using material Durometer hardness. For example, these above modifications may be used when forces of relatively greater magnitudes (e. g., >500 psi) are anticipated. In some embodiments, FSRs are modified to match a range of anticipated forces based on the body weight of the subject.

A single FSR may measure a normal force applied to the sensor. An XYZ digitizing pad that detects position could be used to detect shear motion as well as a normal force in a multiplexed data collection mode. Such information is useful for understanding shoe fit and complications from diseases, such as diabetes, that produce neuropathy and can result in severe body sores and/or a loss of a limb.

In some sensor enable insoles 814, particularly in-shoe force sensing platform or gaming device applications, the sensors are fabricated directly into or onto the insoles. In some embodiments, such as embodiments that are expected to be used outside, it is important that the sensors be protected from abrasion, moisture such as sweat, and creasing, especially in outdoor applications where the subject may run through puddles, rain, etc. Preventing moisture from contacting some types of sensors, such as an FSR, can be especially important because water (and most particularly sweat) is highly conductive and may cause shorting or damage to any electrical system. The resistive characteristics of some commercial resistive materials, such as molybdenum disulfide, change with humidity and the device could be rendered completely inoperable by immersion in liquid, such as water. Therefore, it is desirable to partially hermetically seal the device such that air or other gas may flow out of and into a cavity or space within the sensor-enabled insoles 814 when various forces are both applied and released to the sensor-enabled insoles 814 in order to maintain the functionality of the device. Compression of an FSR air gap may require that the air have a place to escape from the sensor-enabled insole 814 and, correspondingly, when the force is released for there to be a source of return air.

Figure 15:
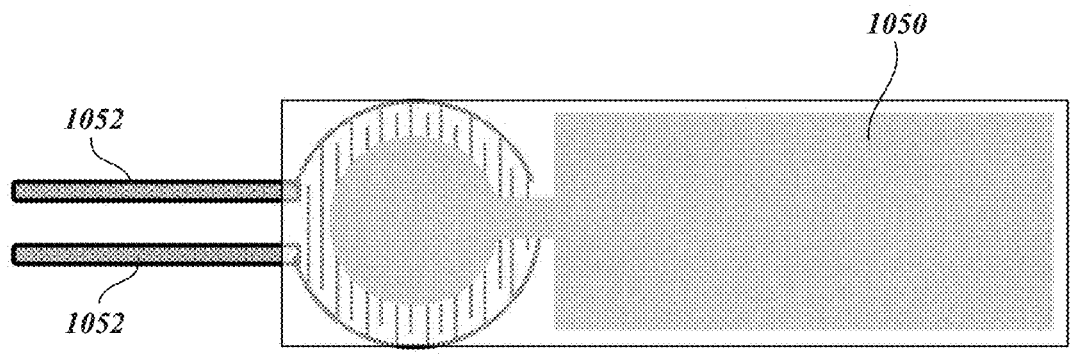
FIG. 15 illustrates a hermetically sealed FSR with air gap venting to an elastic expansion space according to one or more embodiments of the present disclosure.

In some embodiments, FSR sensors may be sealed hermetically or semi-hermetically using silicone encapsulation and/or waterproof/breathable fabrics, such as Gore-Tex™. In some embodiments, sensors and conductive interconnects are printed directly to a known polymer substrate, such as polyethylene terephthalate (PET) or polyethylene naphthalate (PEN); then the fabricated parts are bonded onto an insole insert, such as EVA (ethyl vinyl acetate) foam or silicone rubber suitable for use in FIG. 14. The sensors are then encapsulated or protected with a water-repellant or waterproof material. In some embodiments, sensors and conductive interconnects are printed directly to a known polymer substrate, such as PET or PEN and the fabricated parts are then laminated into the insole insert. The lamination layers would include water-repellant to waterproof materials. Sensors and conductive interconnects are printed directly to a known polymer substrate, such as PET or PEN. Then the part is embedded in silicone rubber or foam, which can form a hermetic seal. Other materials may be selected to form a hermetic seal. In some embodiments, venting to an elastic expansion space in a region that is not specific to actuation results in exchanging cavity air with ambient atmosphere. As illustrated in FIG. 15, an expansion space 1050 provides a controlled atmosphere in the FSR. The expansion space 1050 may be elastic. The spacer layer borders both the printed traces 1052 and the expansion space 1050. In some embodiments, dielectric dots may be printed in the expansion space 1050 to keep the expansion space 1050 open. The expansion space 1050 should be a non-force bearing area so that it may expand normally to the plane of the substrate. It should be large compared to the volume of the FSR cavity so that relatively little motion is required. In some embodiments, the expansion space 1050 is filled with gases besides air to change the dielectric and elastic properties in the expansion space and would permit the use of a liquid pressure medium, if desired.

In some embodiments, sensors and conductive interconnects are printed to an insole using direct-write technologies. The printed parts can then be electrically and chemically insulated from the atmosphere using, for example, ultraviolet (UV) or thermal curing resins and epoxies. Hermetic sealing of sensors and/or interconnects may be accomplished using lamination or encapsulation methods known in the art.

Switches and Interconnects

In some embodiments, for example, involving game input and biomechanic applications, switch contact are used within the insole, shoe, or footwear. Multiple switches are used at different locations within the footwear to detect a pressure that exceeds a particular fixed threshold. Each switch can be configured to switch at different pressure loads. The use of analog sensors such as FSRs or accelerometers requires at least one connection per sensor and a common ground return. Thus, five sensors require a minimum of six signal lines between the sensing platform and processing electronics. The analog sensors can be multiplexed within the footwear; however such multiplexing is accomplished using active electronics installed within the footwear. Digital-to-analog (DA) conversion schemes provide a convenient and superior solution to minimize the number of interconnects between the sensing platform and associated electronics as well as minimize the number of connections required if the switches and electronics are embedded in the footwear. The information of interest is not only which switches are active, but also the sequence and timing of the relative switch openings and closures.

Figure 16:
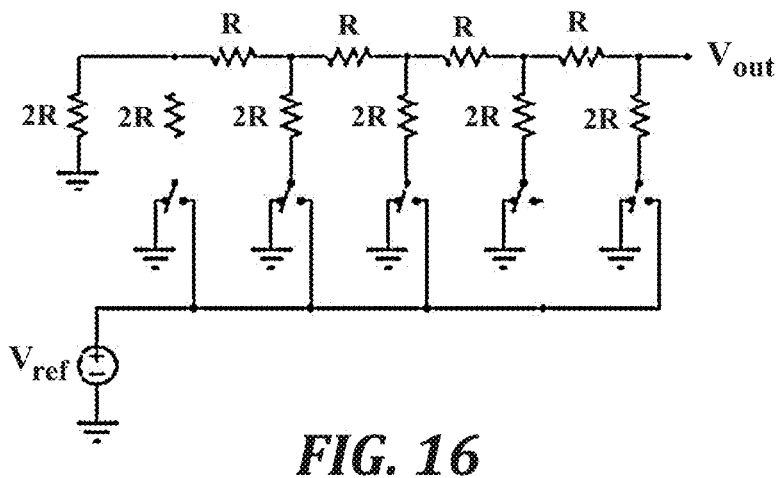
FIG. 16 is a circuit schematic of an R/2R resistive ladder configuration in accordance with various embodiments of the present disclosure.
Figure 17:
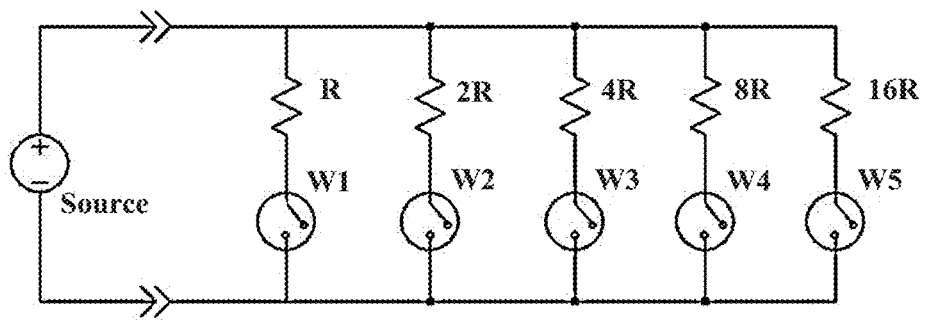
FIG. 17 is a circuit schematic of a binary weighted ladder configuration in accordance with an embodiment of the present disclosure.

FIGS. 16 and 17 illustrate embodiments that are suitable for encoding a combination of switch closures, which may be used to reduce the number of interconnects. FIG. 16 shows a R/2R resistive ladder where a digital input represented by a 1 or 0 at each of the five input locations is the digital input and Vout is an analog output voltage that uniquely represents the particular switch combination. Note that for the topology shown in FIG. 16 the switches are single pole double throw (SPDT). In order to contain the active electronics separate from the switches/resistors three connections: Vout, Vref, and ground are utilized. The configuration shown in FIG. 16 provides a reduction from six to three connections.

A reduction in interconnects can also be obtained by using a binary weighted ladder circuit shown in FIG. 17. In the FIG. 17 circuit, the switches W1-W5 represent individual switches. The Source element is part of the remote electronics and provides either a constant current or constant voltage. The resulting voltage or current (across or through Source) provides a unique indicator of the combination of switches closed. Just two wires connecting the switch/resistor combination in the sensing platform with the remotely located electronics. In an embodiment of foot sensor subsystem 808 that uses the circuit shown in FIG. 17, just resistors and switches are within the sensor-enabled insoles or insertable device 814. In both topologies, additional resistor/switch legs may be added if additional switches are added to counteract external pickup noise sensitivity. The use of interconnects with only two or three signal points reduces cost and increases reliability. In addition, the use of two interconnects opens the possibility of using inductive or capacitive alternating current (AC) coupling and eliminating the need to have a physical connection, further increasing reliability. Also note that for both resistor/switch configurations, relative switch closure timing information is obtained by rapidly sampling the single analog signal to determine if the switch configuration has changed.

Sensors for Angle, Position, and Motion

In some embodiments, additional sensors, such as sensors for determining angle, position, and motion are included in the wearable footwear sensor system 800. Sensors for angle, position, and motion may include accelerometers, gyroscopes, magnetometers, compasses, global positioning systems, and inertial navigation units. Accelerometers and gyroscopes may be embodied in single axis or three axis versions, for example. In some embodiments, nine-axis microelectromechanical systems (MEMS) motion characterization devices, such as three axes each of accelerometers, gyroscopes, and magnetometers, are included in the wearable sensor footwear system 800. Paths of the subject may be tracked by integrating past inputs. The above sensors may be included in the sensor electronics 808 and/or separate from the electronics within the shoe or insole.

Such a diversity of sensors is desirable for determining a wider range of multiple characteristics of the footwear and the subject as enumerated previously.

Additional Sensors

In some embodiments the sensor system 800 includes one or more additional sensors selected from the group consisting of a global positioning system, an accelerometer, a gyroscope, an inertial navigation unit, a force sensor, a shear sensor, a pressure sensor, arrays of pressure sensors, a temperature sensor, a pulse sensor, and a blood pressure sensor. These additional sensors may be included in the insole, in the electronics package, or elsewhere in the shoe. In particular, the temperature in the shoe may be sensed with a thermocouple or thermistor and the dorsal pedal arterial pulse may be sensed by a system and method discussed in connection with FIGS. 18 and 21.

In one aspect the system 800 is further configured to determine a pedal pulse. Doctors and rescue workers often take the pulse at the dorsalis pedis artery because it is strong and readily accessible. Pedal pulses can aid in determining adequate blood flow through the lower extremities. Direct palpation of the dorsalis pedis pulses can rule in or out peripheral vascular disease and is a non-invasive physical exam maneuver that quickly aids in diagnosing.

Figure 18:
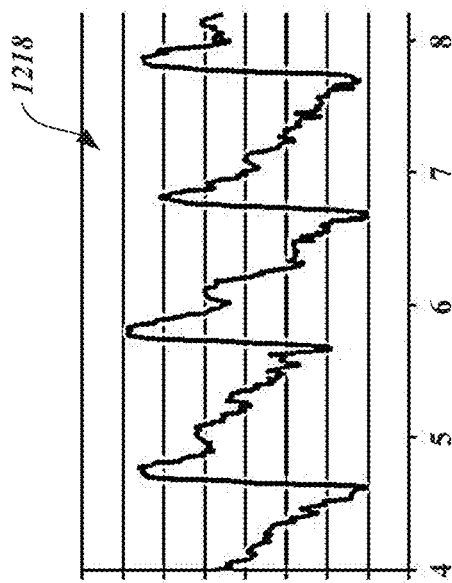
FIG. 18 illustrates force sensors aligned along a blood vessel and an example pulse wave collected from the force sensors.
Figure 18:
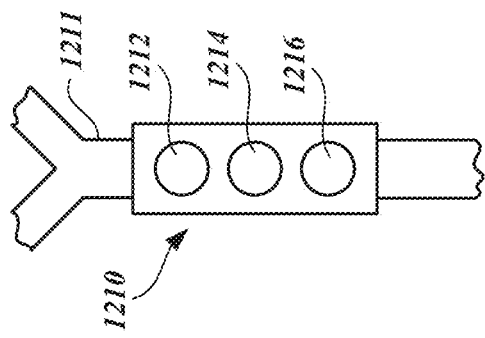
Figure 18:
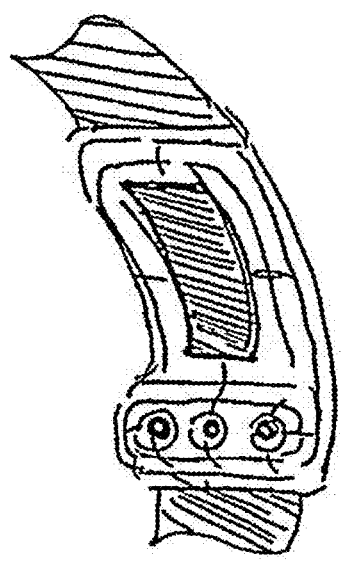
Figure 21:
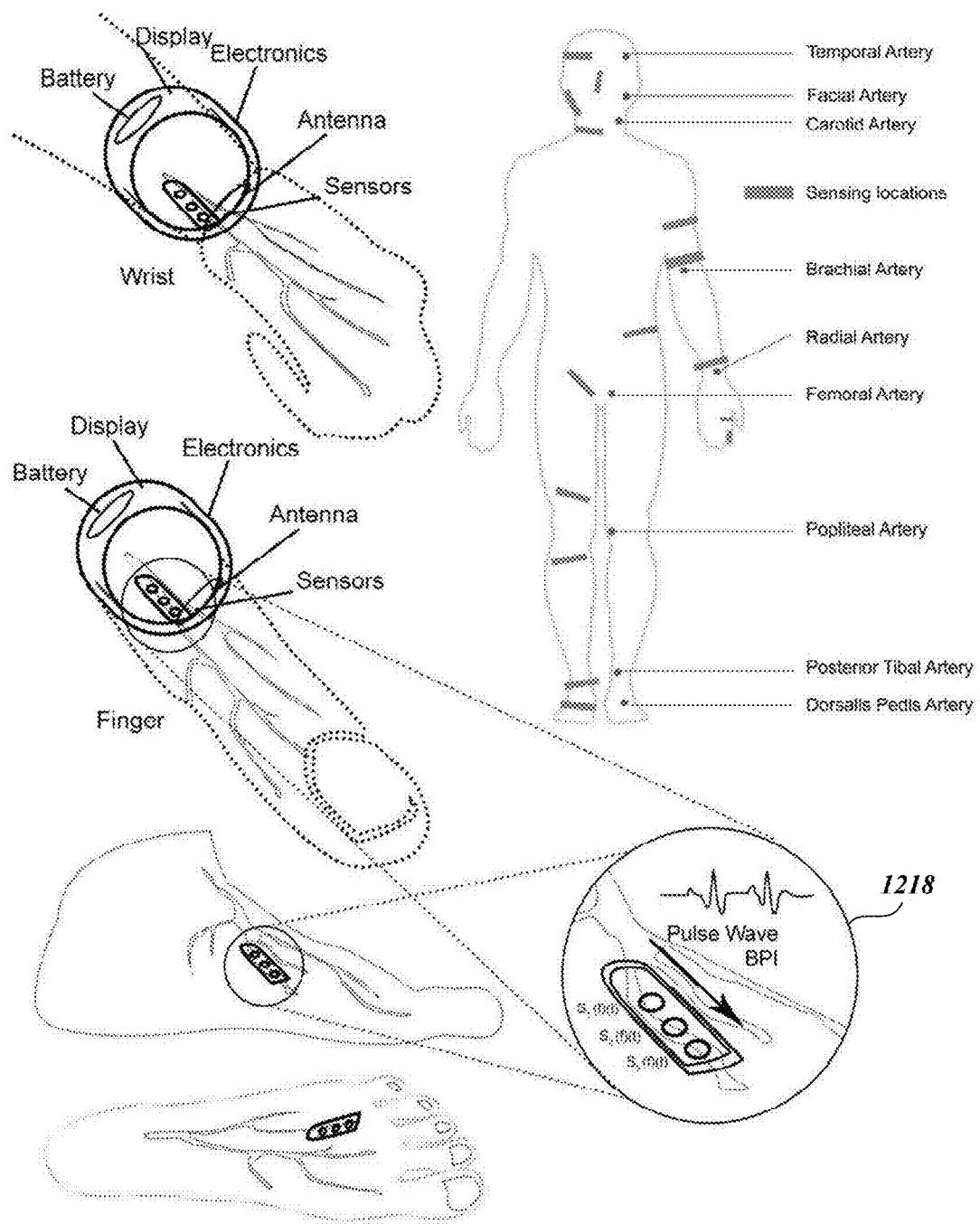
FIG. 21 illustrates various pulse sensors and pedal pulse sensors in accordance with one or more embodiments of the present disclosure.

Current technology captures neither the analog heart rate nor the analog pulse wave to be transmitted live. Referring now to FIGS. 18 and 21, the dorsalis pedis artery 1211 is on the dorsal (top) surface of the foot. In some embodiments, a pulse waveform may be measured at the dorsalis pedis artery 1211 using a method that is non-intrusive with an FSR in or under the tongue of the shoe or in a custom sock.

As shown in FIG. 18, a pulse sensing array 1210 consists of a linear set of pressure sensors 1212, 1214, 1216. In some embodiments pressure sensors 1212, 1214, 1216 include FSRs or piezoelectric transducers aligned along a blood vessel (artery) to pick up the pressure exerted by the blood flow/pulse underneath These pulse signals are used to reconstruct the user's analog pulse and blood pressure curves represented by pulse waveform 1218. Pulse waveform provide real-time information on heart and circulatory system performance. The array 1210 may be functional using just one force sensor; using two or more force sensors in the array 1210 provides better accuracy and measurement reliability.

In one embodiment, a system for measuring a user's analog pulse waveform, such as is shown in FIG. 18, a plurality of FSRs are aligned along a blood vessel, wherein each of the force-sensitive resistors are configured to measure the force on the user's skin between the blood vessel and the force-sensitive resistors, wherein the measured force is indicative of a blood pressure characteristic, and wherein the user's analog pulse waveform is determined by combining the blood pressure characteristic measured by each of the plurality of force-sensitive resistors. Each of the FSRs may be selected and/or optimized individually according to the teaching of this disclosure. In some embodiments, a linear potentiometer may be used instead of an array of sensors. Measured values from the sensor may be sampled at relatively low frequencies such as 100 Hz. In analyzing this data, biometric sensing may be accomplished by comparing the user's analog pulse waveform to a known analog pulse waveform. A method of biometric sensing identifies a user of the system by comparing the user's analog pulse waveform to a known analog pulse waveform. In analyzing this data, biometric sensing may be accomplished by comparing the user's analog pulse waveform to a known analog pulse waveform. Gait and or pulse waveform can be measured on a subject over a defined period of time to provide the system with a baseline for bio-authentication by extracting features of the collected values such as frequencies, profiles. and amplitudes using shape based analysis, and comparing them to a database of complied approved features and values.

In one embodiment, a system for measuring a subject's analog pulse waveform comprises a plurality of force-sensitive resistors (FSR) positioned along a blood vessel, wherein each FSR is configured to measure a force exerted by the blood vessel, where the measured force of the blood vessel is indicative of a blood pressure characteristic, and wherein the subject's analog pulse waveform is determined by combining the measured blood pressure characteristics of each of the plurality of force-sensitive resistors. In one aspect, the system is further configured to determine a pedal pressure. In another aspect, the system is part of a ring. In another aspect, the system is attached to a wrist. In another aspect, the system is on a patch or a substrate that is flexible or stretchable.

Electronics

Figure 19:
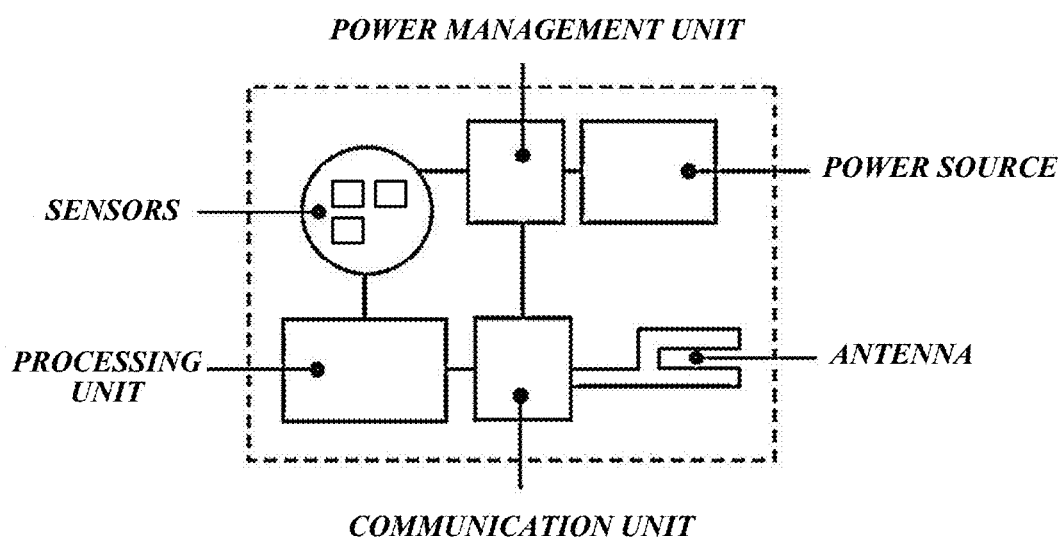
FIG. 19 is a block diagram of sensor electronics in accordance with one or more embodiments of the present disclosure.

Referring back to FIGS. 8 and 9, footwear electronics 810 may be attached inside or outside of footwear 802. Referring now to FIG. 19, a block diagram of an embodiment of footwear electronics 810 is shown. Footwear electronics 810 includes sensors such as accelerometers or other sensors discussed herein, a power source for powering the sensors, a power management unit, a processing unit, a communications unit, and an antenna. The power source is typically a battery, but other types of power sources such as solar cells or kinetic energy may be used. In some embodiments, electronics may include memory or storage for saving various data measured by the sensors.

The electronics and battery may be rigid such that they do not fit comfortably in a foam or silicone insole; therefore, the electronics need to remain connected in a way that does not cause discomfort to the user such as on an outer surface of the footwear 802. In some embodiments that using flexible printed electrical connections are used in lieu of wires such as is shown in FIG. 14, many small connection traces can be drawn to a rigid circuit board and battery positioned outside or embedded in the footwear 802. To adapt to a variety of types of footwear 802, a flexible tail is drawn up the inside of the quarter of a shoe so that the sensor package may be attached to the outside of the shoe. This allows for an interface to accommodate nearly every shoe style while preventing any discomfort. It also prevents any issues when sliding the foot into the shoe.

The electronics 810 may be covered in a small waterproof container as is shown in FIGS. 8 and 11. By attaching a thin shape memory material to the flexible circuit interconnection region, the flex circuit can rigidly grip the edge of the shoe. The electronics 810 rests outside the footwear 802. The positioning of the electronics 810 shown in FIG. 11 is also advantageous because the electronics 810 are less likely to make contact with electronics 810 of other footwear 802, which could damage the electronics if the feet come together. In some embodiments, the electronic 810 will include a cover that hermetically seals with the electronics with a seal around the printed flex tail.

Alternatively, the electronics 810 may be packaged in a component inserted in a cavity in a sole or a heel counter of footwear 802. In this case, the interconnects 812 must be made to insert through the shoe material or otherwise connect the electronics 810 with the sensor-enabled insoles 814 without being obtrusive to the wearer.

Communications and Data Synchronization

The wearable footwear sensor system 800 may include multiple communication paths between devices. For example, two or more foot sensor subsystems 808 and the master device, such as a smart device 822, mobile electronic device 824, or a personal computer 826, may be configured to communicate wirelessly with one another. In addition, the master device may also be configured to communicate with other devices such as a mobile computing device, over a cellular phone network, a satellite network, or a wireless hotspot. Wired communication is possible in the laboratory, between the master device and other devices, but it is preferable for the foot sensor subsystem 808 and the master device to communicate wirelessly. Wireless communication may be with electromagnetic, optical, or acoustic paths. As mentioned above, wireless communication may utilize the Bluetooth standard since many master devices are already so enabled. Wireless communication can also be performed inductively, with blinking IR lights, ultrasonic bursts, or other RF methods using different frequencies or protocols. It could be done using a free band, such as is used at 300 MHz for wireless thermometers that broadcast periodic synchronization pulses.

Data synchronization from multiple wireless devices determines characteristics of an activity. While having the devices all hardwired together allows for synchronization, it is also extremely cumbersome and obtrusive to the wearer. In some embodiments, each shoe would have an independent wireless transceiver and additional wireless-enabled accelerometer/gyroscope sensors at other body locations anticipated 1) near the body center of mass to remove whole body effects and 2) at various points on the limbs to show the body dynamics of the hip, knee and ankle. Additional position/motion sensors may be included in master devices such as smart phones, smart watches, smart glasses, etc. The "master device" could be a smart phone, personal digital assistant, MP3 player, smart watch, smart glasses, tablet computer, other computer or any device equipped with processing, communications and timing capabilities. The software on the master device can accept data and communicate with multiple wireless devices. Data can be stored locally on the master device or stored at a remote server/data center.

The master devices collect data from individual data sources and transmit the data to a master device via a wireless network or communication protocol. The data sources could be any set of sensors wired to a single wireless transceiver henceforth termed a "device." The devices would contain planar antennas that receive the power from the transmission board. The sensors could be one or more accelerometers, FSRs, gyroscopes, and other sensors. FSRs would be external to the transceiver package, but accelerometers and gyroscopes could be internal and located directly on the printed circuit board. Secondary accelerometers/gyroscopes could be external to the electronics package to elucidate, for example, angular motion of the foot.

Specifically, data collection is synchronized to an internal clock within master device. When synchronized to the master device, a device will be configured to output an associated measured data with a relative time. All data collected by the foot sensor subsystem 808 and communicated to the master device contains the time stamp or tag from the foot sensor subsystem 808 clock. The master device is configured to synchronize the clocks of multiple individual devices, such as the foot sensor subsystem 808, so that data collected from foot sensor subsystem 808 may be aligned in time with the master device. Data from the individual devices is commonly sent in a burst mode so that the wireless network receiver and transmitter can be powered off for a majority of the time to reduce power consumption. However sending in burst mode makes time synchronization between foot sensor subsystems 808 an issue.

By communicating in burst mode rather than real time, the individual devices can be very low power with long battery life. To make the devices hermetically sealable, the devices may be made with no connection for battery charging, but instead be inductively charged/recharged by placing the device on an inductive power transmission board or mat.

In another aspect the sensor system is interfaced and time correlated with additional sensors at body locations other than the feet. Additional accelerometer/gyroscope sensors at other anatomical locations could be secured with belts/straps/hook and loop (Velcro) or in pockets in articles of clothing to other areas of interest including the back of the waist, front of the waist, and portions of the limbs. These devices will be in wireless communication with a central device to capture and coordinate different body movements. One accelerometer/gyroscope sensor could be a smart phone that also contains a global positioning system (GPS), which provides an absolute time stamp (see, e.g., FIG. 20).

In one aspect the system comprises a pulse sensor that is part of a ring. In another aspect the system comprises a pulse sensor that is held on the wrist. In another aspect the device is on a patch or a substrate that is flexible and/or stretchable.

Additional pulse sensing devices, according to the teaching of the present disclosure, may be placed at additional anatomical locations per FIG. 21 and put in communication and synchronization with the master device.

Other Applications

Force and acceleration sensors are useful in other applications besides footwear, specifically athletics and more specifically high-impact sports such as football, where impact injuries, including concussions, are common and must be diagnosed quickly and ameliorated with good design of protective equipment, which is bulky and readily allows for incorporation of sensors.

Figure 22:
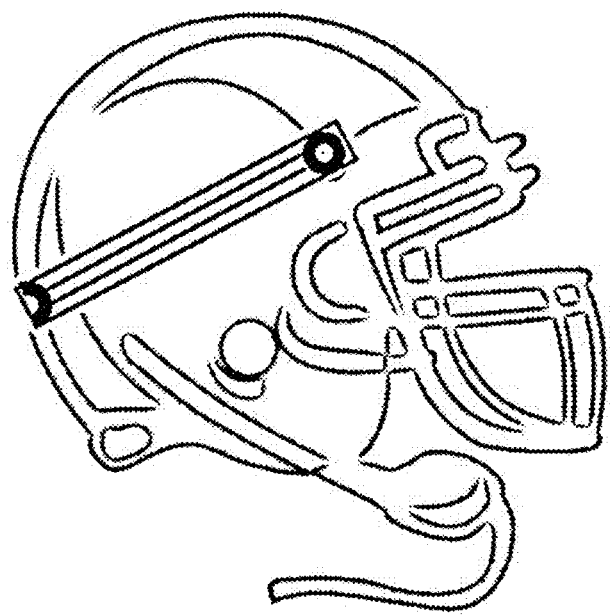
FIG. 22 illustrates sensor embedded on a football helmet in accordance with embodiments of the present disclosure.

In one aspect the optimized FSR devices are adhered to or embedded in a piece of athletic equipment. In another aspect, the athletic equipment is a helmet or protective padding. In some embodiments, football helmets may be designed as shown in FIG. 22 with FSRs on inner and outer surfaces and accelerometers with wireless transmission capability to be compared with accelerometers in shoulder pads. Any other protective equipment intended to minimize contact force to the wearer may be similarly instrumented, e.g., shoulder pads, knee pads, elbow pads, hip pads, shin guards, forearm guards, wrist guards, hand guards, thigh boards, ear guards, rib pads, body armor, "flak" jackets, trunk/thorax protection, neck rolls, athletic cups, face guards, mouth guards, throat guards, protective shoes/boots, ankle braces, knee braces, etc.

In another aspect, the athletic equipment comprises one or more of the following: a ball, a bat, a golf club, a bicycle seat, a snow board, and a skateboard.

Figure 26:
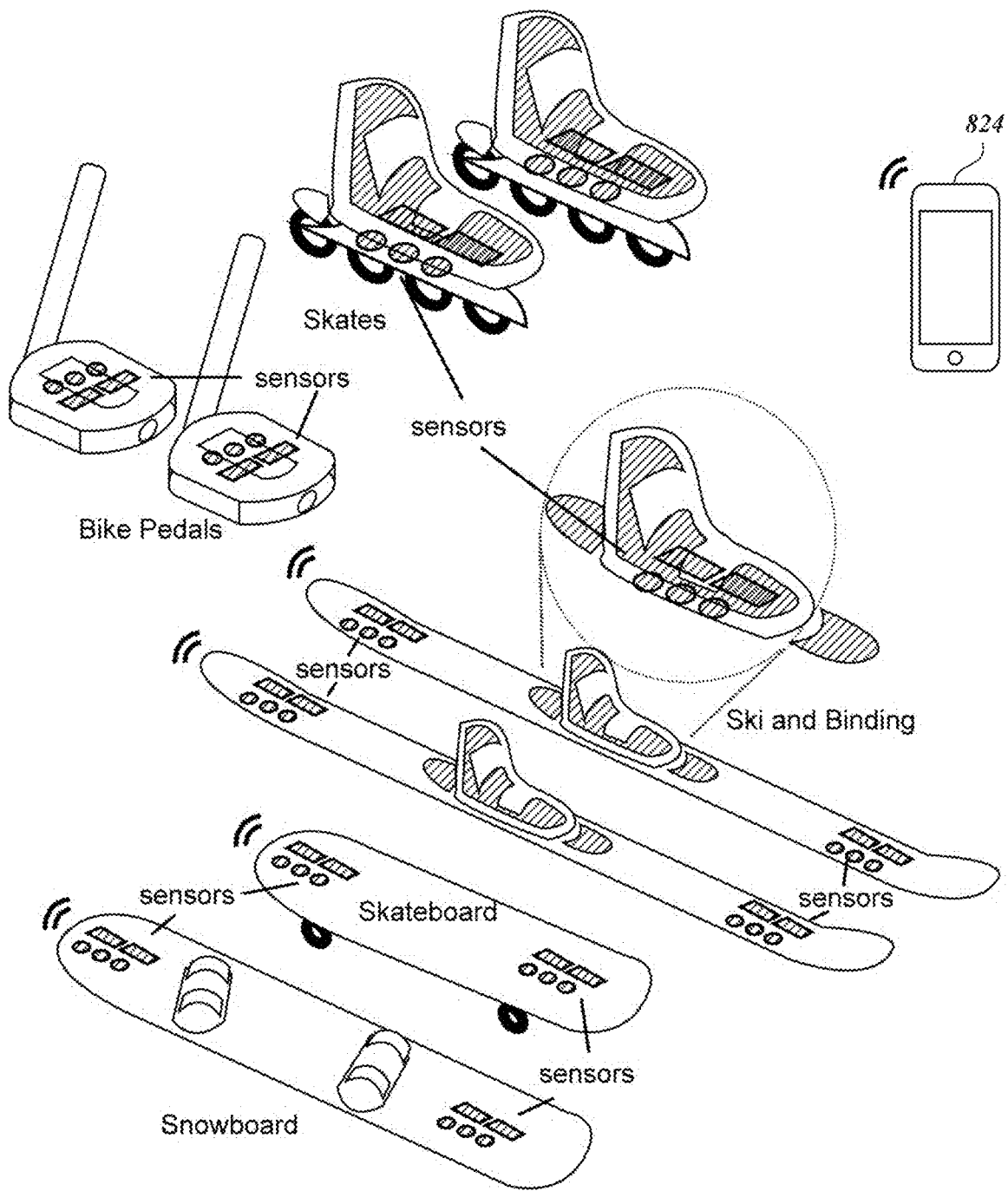
FIG. 26 illustrates various athletic equipment embodiments that include FSRs in accordance with one or more embodiments of the present disclosure.

In other embodiments, embedded sensing systems on boards and skateboards, as shown in FIG. 26, can provide useful information for training and performance monitoring for the subject.

Figure 23:
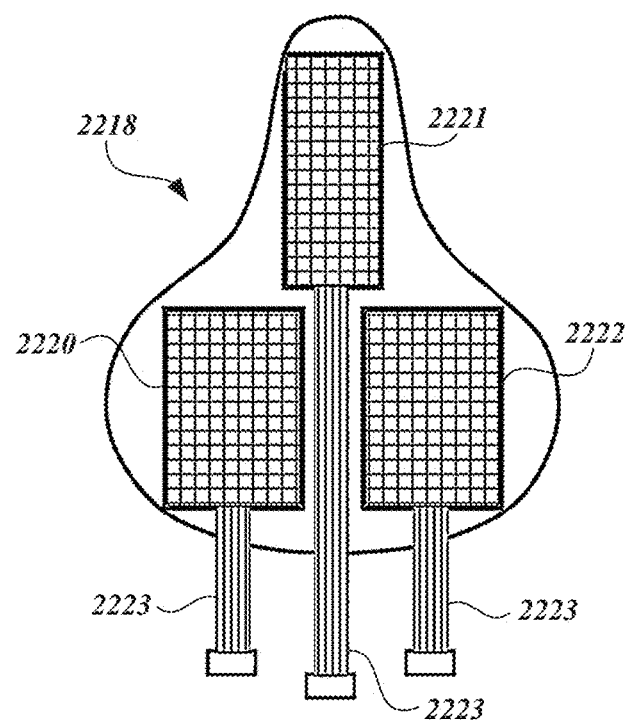
FIG. 23 illustrates a bicycle seat with strategically placed FSR sensors.

As shown in FIG. 23, a bicycle seat 2218 may be instrumented with FSRs or XYZ digitizer pads 2220, 2221, 2222 connected to interconnects 2223. Bicycle seat 2218 may be used for fitting to a rider or identifying a location of excess pressure and potential neuropathy. Sports equipment including balls, bats, golf clubs, etc. can be instrumented for training and measurement purposes. Sports shoes of all types can be instrumented with FSRs on surfaces other than the sole to measure lateral force and kicking force (exterior of shoe) as well as the instrumentation described previously.

Prior Art Example #1—Single Sensor Bluetooth Enabled Device

Nike's Nike+ Sport Sensor consists of a single device place in a compartment in the sole of one shoe. Only a single data set is communicated to a Bluetooth enabled master device such as a smart phone, so data correlation is not required.

Prior Art Example #2—Commercial FSRs Attached to Insoles

A number of prior art sources have attached commercially available force-sensitive resistors to standard shoe insoles. No attempt to vary the dynamic range or to print the FSRs on a common substrate has been documented. Separate shoe devices transmitted using radio frequency signals not in burst mode, which is how timing is accomplished, but also uses excessive amounts of power.

Prior Art Example #3—Large Arrays of FSRs

The Tekscan F-Scan Wireless system has an array of 960 sensors all connected to a single wireless node by wires, which is how timing is accomplished, but is very obtrusive to the wearer and may affect the gait. The sensor array is cut to fit a shoe. There are versions with sensor ranges from 50 to 125 psi with no apparent dynamic range optimization across the array. It is marketed to physicians rather than individuals.

Example #4—Screen Printed Three Shunt Mode FSRs Shape Matched to Shoe Sole

A set of three layers comprising three force-sensitive resistors printed simultaneously in parallel and assembled as a single unit as follows: An 800 □ sheet resistance molybdenum disulfide layer screen printed on a 0.005" thick heat-stabilized polyester substrate in 0.5" diameter circles under three anatomical locations: the head of the first metatarsal bone (ball of the foot), the base of the fifth metatarsal bone (outer arch), the center of the calcaneus (center of heelbone).

Conductor traces 0.015" wide or wider from each set of interdigitated fingers are simultaneously screen printed in silver paste to the heel. There are no dielectric dots printed in this design. All three polymer layers are cut in the shape of the top of a shoe sole with the conductor traces terminating in a tail that extends from the heel portion of the shape to allow the conductor lines to enter the rigid heel portion (counter) of the shoe where they attach to connectors.

This sensor system is suitable for a 6-foot tall, 150-pound man, wearing men's size 10½ shoes. This central combination would be suitable for a wide range of weights and shoe sizes. In circumstances where there are greater forces, a 0.030" spacing with 0.015" fingers would be preferred. An individual over 200 pounds may also require slightly thicker spacers (e. g. 0.007" and 0.011"). It is not anticipated that height, gender, and shoe size will have as strong an effect as weight.

Example #5—Screen Printed Three Shunt Mode FSR Shape Matched to Shoe Sole for a Smaller Subject For a smaller subject, such as a female of 5 foot 2 inches, weighing 115 lbs., and wearing women's size 7½ shoes, the sensor configuration would consist of three layers comprising three force-sensitive resistors printed simultaneously in parallel and assembled as a single unit as follows: an 800 □ sheet resistance molybdenum disulfide layer screen printed on a 0.005" thick heat-stabilized polyester substrate in 0.5" diameter circles under three anatomical locations: the head of the first metatarsal bone (ball of the foot), the base of the fifth metatarsal bone (outer arch), the center of the calcaneus (center of heelbone). A split thickness spacer comprised of 3M 467MP acrylic with adhesive on both sides and circular cavities cut in registry with the same anatomical locations as in 1a, b, c with the following thicknesses and internal diameters: the head of the first metatarsal bone 0.004" thick, 0.45" diameter cavity, the base of the fifth metatarsal bone 0.007" thick, 0.45" diameter, the center of the calcaneus 0.007" thick, 0.40" diameter.

Each hole has an air vent cut to exit between the conductor lines. Interdigitated conducting finger traces 0.015" wide, screen printed in a circular pattern 0.5" in diameter with silver paste onto a second 0.005" thick heat-stabilized polyester substrate in registry with the same anatomical locations as in 1a, b, c with finger spacing: the head of the first metatarsal bone 0.025" spacing, the base of the fifth metatarsal bone 0.020" spacing, the center of the calcaneus 0.025" spacing, conductor traces 0.015" wide or wider from each set of interdigitated fingers are simultaneously screen printed in silver paste to the heel.

Example #6—Shear Sensor

A set of FSRs where instead of a simple FSR, each device is a square or rectangular matrix array (e.g., 2×2, 2×3, etc.) XYZ digitizer pad allowing the determination of both normal force and shear motion of the point of greatest pressure when the output is read out in two different time-multiplexed patterns as is familiar to those skilled in the art. The dynamic range across the array can be varied by varying the dielectric dots in number and thickness or other varying other FSR characteristics/parameters as discussed herein.

Example #7—FSR/Accelerometer/Wireless Combination

An optimized set of FSRs per Example #4 wired with tinned female connectors to a printed circuit board containing a three-axis accelerometer and a Bluetooth chip with firmware enabling communication and control with a smart phone. Data collection is synchronized to an internal clock within the Bluetooth chip that is set from the smart phone global positioning system clock. Each data set contains voltage readings from the three FSRs, accelerometer readings from all three axes of the accelerometer, and a time stamp for the time the data was measured (not the time transmitted). The accelerometer and electronics package is attached to the outside lace area of the shoe with a spring steel clip, encapsulated in a cavity in the heel box, a cavity in the arch of the shoe, a pocket in the tongue of the shoe, or plugged into a connector on the back of the shoe (counter or back seam), accommodated in other locations. Each shoe is so equipped. A separate Bluetooth-enabled accelerometer with no FSRs is attached to the back of the subject's belt with a spring steel clip. The data from all three devices may be correlated at any level of processing as a result of the accurate time stamps.

Example #8—Instrumented Football Helmet

A football helmet experiences substantially different forces than the plantar surface of the foot and therefore requires different designs. Sensors on the bottom of a shoe are expected to have a dynamic range that doubles between walking and running, but are not expected to exceed 200 psi. The exterior of a football helmet must withstand up to 1100 psi of force, but communicate as little of that as possible to the skull, most likely in the 100 psi range, but with a need to have better accuracy. The range of forces experienced by a helmet are more uniform than those experienced by a foot; therefore the split spacer design is not required. Internal forces at the temples should be lower as both physiology and helmet design protect these more vulnerable areas to a greater degree than the back of the head. Dielectric dots in the exterior sensors extend the range strongly while allowing the other design parameters to stay substantially the same.

For a football helmet, this exemplary device has two sets of four layers comprising three force-sensitive resistors printed simultaneously in parallel and assembled as a single unit as follows: an 800Ω sheet resistance molybdenum disulfide layer screen printed on a 0.005" thick heat-stabilized polyester substrate in 0.5" diameter circles under three anatomical locations: the back of the skull, the right side of the skull over the temple, the left side of the skull over the temple.

A 0.009" thick spacer comprised of 3M 467MP acrylic with adhesive on both sides and circular cavities cut in registry with the same anatomical locations as in 1a, b, c with the following internal diameters: the back of the skull 0.35" diameter, the right side of the skull over the temple 0.40" diameter, the left side of the skull over the temple 0.40" diameter. Each hole has an air vent cut to exit between the conductor lines. Interdigitated conducting finger traces 0.015" wide screen printed in a circular pattern 0.5" in diameter with silver paste on a second 0.005" thick heat-stabilized polyester substrate in registry with the same anatomical locations as in 1a, b, c with finger spacing as follows: the back of the skull 0.025" spacing, the right side of the skull over the temple 0.020" spacing, the left side of the skull over the temple 0.020" spacing.

For sensors on the exterior of the helmet, dielectric dots in a square array with x and y spacings of 0.1" are printed over the areas of the fingers to increase the dynamic range for up to 1100 psi for football helmet ratings. Conductor traces 0.015" wide or wider are simultaneously screen printed in silver paste from each set of interdigitated fingers to a connecting tail located at the back of the head.

Actuators made of silicone rubber sheet 0.016" thick and 0.5" diameter with adhesive on one or both sides applied over the FSR regions to supply a more generic/repeatable force actuator that will not change over time as is typical of foam padding. All three polymer layers are cut in the shape of a strip with a tail at the back of the head to allow the conductor lines to the electronics encased in the padding of the helmet where they attach to tinned female connectors. These are laminated to the outside of the helmet and the inside of the padding and connected to a printed circuit board containing a three-axis accelerometer and a Bluetooth chip with firmware enabling communication and control with a recording device with a separate accelerometer in the back of the shoulder pads. Data collection is by readout to a wireless-enabled computer on the sidelines and is synchronized to internal clocks within the Bluetooth chips that are set from the master computer and correlated with the game clock. Each data set contains voltage readings from the six FSRs, accelerometer readings from all three axes of the helmet and shoulder pad accelerometers and a time stamp for each device. The data may be correlated at any level of processing as a result of the accurate time stamps.

TABLE I illustrates a variation of FSR parameters for a foot (Example #4) and helmet locations (Example #8) to optimize dynamic range.

| Location | Resistivity | Substrate Thickness | Spacer Thickness | Cavity Diameter | Trace Width | Trace Spacing | Dielectric Dots |
|---|---|---|---|---|---|---|---|
| Ball of foot | 800 Ω | 0.005" | 0.005" | 0.040" | 0.015" | 0.030" | No |
| Arch | 800 Ω | 0.005" | 0.009" | 0.040" | 0.015" | 0.025" | No |
| Heel | 800 Ω | 0.005" | 0.009" | 0.040" | 0.015" | 0.030" | No |
| Helmet back int. | 800 Ω | 0.005" | 0.009" | 0.035" | 0.015" | 0.025" | No |
| Helmet side int. | 800 Ω | 0.005" | 0.009" | 0.040" | 0.015" | 0.020" | No |
| Helmet back ext. | 800 Ω | 0.005" | 0.009" | 0.035" | 0.015" | 0.025" | Yes 0.1" |
| Helmet side ext. | 800 Ω | 0.005" | 0.009" | 0.040" | 0.015" | 0.020" | Yes 0.1" |

Example #9—Controller for Games

In one aspect the sensor system is interfaced with an electronic game, such as a console game, computer game, or mobile game. The present disclosure discussed in this document can be used as a controller for games, role games, strategic games, video games, dancing, and gamification of health, for example. In another aspect, the two or more determined characteristics are converted using a computing device to at least one of an output signal for moving an avatar in a virtual world or an output signal corresponding to an output signal from a computer input device including a keyboard, a mouse, or a joystick. In the case of video games, the system can interface with conventional computing devices (fixed and mobile) where the different sensors on the footwear are mapped into regular controllers, mouse, joystick, and keyboard (FIG. 24). The present disclosure opens opportunities for novel gaming experiences by allowing playing outside of houses and buildings, and geotag scores and positions (FIG. 25). Any footwear becomes a game controller for the real world. In this case, the system can communicate live with a computing device or record data internally for later processing.

Example #10—Body Movement

It has been found that state-of-the-art game controllers or devices that encourage user body movement actually cannot enforce it. They cannot discern between a major body movement and a subtle hand movement. Thus, they are easily deceived by tricks performed by the user. For example, Nintendo Wii controllers cannot differentiate between an arm and a two-finger movement or a walk and an arm movement. The same issue applies on smartphone accelerometers and fitness wrist monitoring devices. The wearable footwear described on this embodiment can be configured for each user weight. This feature reduces any possibilities of tampering with the device (cheating) for operation. To activate the sensors, the user's weight is used to define mechanically the "initial sensor state."

To enforce body movement, the present disclosure uses the weight of the user as input to activate the controller. In the case of switches, multiple devices can be placed on top of each other (overlay). In that case, one of the switches is set to be activated by the user's weight. Once the electronics detects this signal, then the other sensors become functional and start to operate. In the case of FSR devices, the sensors are optimized to operate above a threshold value defined by the user's weight. This process can be performed using a calibration tool and variable bias.

Example #11—Dancing

In the case of dancing, a person, a couple, or a group of people can use the sensing platform to evaluate and analyze their performance. This situation can occur in person, over the internet, on TV, or on any other type of situation when there is live communication. The dancers can evaluate their movements as a function of time. If required, additional sensing points on the user's body can be installed and networked as indicated in FIG. 20 to produce a more accurate body movement representation.

In addition to the mentioned cases, there are other potential applications of the sensing platform: Controller for third activities such as timeline navigator on video/music edition, machine controller, controller for robotics and remotely operated devices, and actuator controller for additional degrees of freedom.

In another aspect, the sensor system is interfaced with a workforce-monitoring system for load on movement assessment. In this case, the wearable sensing platform is used for monitoring personnel (such as courier, warehouse workers, and soldiers), for example, to assess weight load, balance, and the possibility of physical overload due to cargo manipulation in industrial use. A crew management application can be used to reduce back injuries on the personnel and avoid insurance premium increases by monitoring attrition of the workforce.

In some embodiments, an avatar can be powered based on physical activity. The more a person moves, the more the power or skills his/her avatar gets. The avatars can compete on virtual challenges or games when paired by their users.

The system 800 can be used as an outdoor controller for use with foot-based sports hardware such as skateboards, skies, skates, surfboards, bicycles, and shoes. A user may play with these goods and the data can be aggregated to standard console videogames to earn extra points, lives, or skills.

As mentioned above, in another aspect, the sensor system 800 is interfaced with a biomechanical analysis system. Embodiments of the present disclosure may use as an enhanced biomechanics tracker and may be installed on any kind of footwear such as running shoes, sky booths, hiking boots, and sandals. This allows the user to perform any kind of activity such as parkour, skateboarding, running, jumping, walking, spinning, hiking, playing role games, playing life strategic games, and so on, and to quantify his/her physical activity for fitness and performance assessment (See, e.g., FIG. 25).

Some embodiments can be used for locomotion rehabilitation and biomechanical analysis. In another aspect, the sensor system is interfaced with a speaker, earbuds, headphones, or sound generation device to provided aural feedback to the subject. Such aural feedback can be used for the user interactions. For example, sound samples can be linked to specific foot actions such as jumping, leaning, slow walk, fast walk, and squats. In this case, audio can be produced using devices such as speakers, earbuds, and headphones.

While illustrative embodiments have been illustrated and described, it will be appreciated that various changes can be made therein without departing from the spirit and scope of the invention.

The embodiments of the invention in which an exclusive property or privilege is claimed are defined as follows:
1. A footwear system, comprising:
   two separate foot sensor subsystems each carried by a shoe of a subject and each comprising:
   at least one force sensor configured to measure a force at at least one predetermined anatomical location on a foot, and
   footwear electronics coupled to the at least one force sensor,
   wherein each foot sensor subsystem is operatively coupled with a computing device;
   the footwear system further comprising a non-volatile memory that carries programming instructions, which, when executed, cause the foot sensor subsystem to:
   (a) define subject's weight based at least in part on a weight distribution across a foot, a total weight applied to the foot, and a partial weight applied to the foot;
   (b) transfer the subject's weight data to the computing device;
   (c) activate the computing device in response to the subject's weight data;
   (d) establish an initial sensor state based on the subject's weight data; and
   (e) reduce tampering with the computing device by:
   activating at least one foot sensor subsystem by the footwear electronics based on the subject's weight data corresponding to the initial sensor state, and not activating the at least one foot sensor subsystem by the footwear electronics based on the subject's weight data lacking correspondence with the initial sensor state.

2. The system of claim 1, further comprising at least one sensor device selected from a group consisting of an accelerometer and a gyroscope.

3. The system of claim 2, further comprising a clock configured to generate time stamped device data for each sensor device that includes a relative time that the device data was generated, wherein each clock is synchronized by communication with a master device.

4. The system of claim 1, wherein the footwear electronics are attached to an outside surface of the corresponding shoe.

5. The system of claim 1, further comprising a data processing system in communication with both of the foot sensor subsystems, wherein the data processing system is located separately from at least one of the foot sensor subsystems.

6. The system of claim 1, further comprising a substrate that carries the at least one force sensor, wherein the substrate comprises an elastic expansion space adjacent to the at least one force sensor, and wherein the expansion space enables the at least one force sensor to expand into the expansion space.

7. The system of claim 6, wherein the expansion space expands normally with reference to a plane of the substrate.

8. The system of claim 6, wherein the expansion space includes dielectric dots that keep the expansion space open.

9. The system of claim 1, wherein the at least one force sensor includes switches that detect a pressure that exceeds a predetermined pressure threshold.

10. A footwear system, comprising:
two separate foot sensor subsystems each carried by a shoe of a subject and each comprising:
at least one force sensor configured to measure a force at at least one predetermined anatomical location on a foot, and
footwear electronics coupled to the at least one force sensor,
wherein each foot sensor subsystem is operatively coupled with a computing device;
the footwear system further comprising a non-volatile memory that carries programming instructions, which, when executed, cause the foot sensor subsystem to:
(a) define subject's weight based at least in part on a weight distribution across a foot, a total weight applied to the foot, and a partial weight applied to the foot;
(b) transfer the subject's weight data to the computing device;
(c) activate the computing device in response to the subject's weight data;
(d) establish an initial sensor state based on the subject's weight data; and
(e) reduce tampering with the computing device by:
activating at least one foot sensor subsystem by the footwear electronics based on the subject's weight data corresponding to the initial sensor state, wherein the subject's weight data is detected by one or more switches, and
not activating the at least one foot sensor subsystem by the footwear electronics based on the subject's weight data lacking correspondence with the initial sensor state, wherein the subject's weight data is detected by one or more switches,
wherein the switches are arranged as a binary weighted ladder circuit.

11. The system of claim 1, wherein the sensor system is configured to be used outdoors.

12. The system of claim 1, wherein the sensor system is configured to be used indoors.

13. A pair of footwear, comprising:
a footwear system having two separate foot sensor subsystems each carried by a piece of footwear of a subject, each foot sensor subsystem comprising:
at least one force sensor configured to measure a force at at least one predetermined anatomical location on a foot, and
footwear electronics coupled to the at least one force sensor,
wherein each foot sensor subsystem is operatively coupled with a computing device;
the footwear system comprising a non-volatile memory that carries programming instructions, which, when executed, cause the force sensitive resistors to:
(a) define subject's weight based at least in part on a weight distribution across a foot, a total weight applied to the foot, and a partial weight applied to the foot;
(b) transfer the subject's weight data to the computing device;
(c) activate the computing device in response to the subject's weight data;
(d) establish an initial sensor state based on the subject's weight data; and
(e) reduce tampering with the computing device by:
activating at least one foot sensor subsystem by the footwear electronics based on the subject's weight data corresponding to the initial sensor state, and
not activating the at least one foot sensor subsystem by the footwear electronics based on the subject's weight data lacking correspondence with the initial sensor state.

14. The footwear of claim 13, further comprising a data processing system in communication with both of the foot sensor subsystems, wherein the data processing system is located separately from at least one of the foot sensor subsystems.

15. The footwear of claim 14, wherein the data processing system is interfaced with at least one of the following:
a display device;
an electronic game, the electronic game including one or more of a console game, a computer game, or a mobile game;
a speaker, earbuds, headphones, or sound generation device to provide aural feedback to the subject;
a workforce monitoring system for load on movement assessment;
a biomechanical analysis system; and
additional time-correlated sensors at body locations other than the feet.

16. The footwear of claim 13, wherein each sensor subsystem further comprises one or more additional sensors selected from the group consisting of a global positioning system, an accelerometer, a gyroscope, an inertial navigation unit, a force sensor, a shear sensor, a pressure sensor, arrays of pressure sensors, a temperature sensor, a pulse sensor, and a blood pressure sensor.

17. The footwear of claim 13, wherein at least one of the sensor subsystems comprises a plurality of digital switches configured to detect pressure, the plurality of digital switches being positioned adjacent to a bottom of the foot of the subject.

18. The footwear of claim 13, wherein the programming instructions, when executed, further cause the foot sensor subsystem to generate an output signal for moving an avatar in a virtual world.

19. The footwear of claim 13, wherein the programming instructions, when executed, further cause the foot sensor subsystem to generate an output signal corresponding to a keyboard output signal.

20. The footwear of claim 13, wherein the footwear electronics are attached to an outside surface of the corresponding piece of footwear.

* * * * *